US009456737B2

(12) United States Patent
Pascal

(10) Patent No.: US 9,456,737 B2
(45) Date of Patent: Oct. 4, 2016

(54) IN-VIVO IMAGING DEVICE AND METHOD FOR PERFORMING SPECTRAL ANALYSIS

(75) Inventor: Amit Pascal, Haifa (IL)

(73) Assignee: GIVEN IMAGING LTD., Yoqneam (IL)

( * ) Notice: Subject to any disclaimer, the term of this patent is extended or adjusted under 35 U.S.C. 154(b) by 236 days.

(21) Appl. No.: 13/885,080

(22) PCT Filed: Nov. 16, 2011

(86) PCT No.: PCT/IL2011/050014
§ 371 (c)(1),
(2), (4) Date: May 13, 2013

(87) PCT Pub. No.: WO2012/066553
PCT Pub. Date: May 24, 2012

(65) Prior Publication Data
US 2013/0231536 A1    Sep. 5, 2013

Related U.S. Application Data

(60) Provisional application No. 61/414,060, filed on Nov. 16, 2010.

(51) Int. Cl.
*G06K 9/00* (2006.01)
*A61B 1/04* (2006.01)
(Continued)

(52) U.S. Cl.
CPC ........... *A61B 1/041* (2013.01); *A61B 1/00186* (2013.01); *A61B 1/0638* (2013.01); *A61B 1/0684* (2013.01)

(58) Field of Classification Search
CPC ...................................................... A61B 1/041
See application file for complete search history.

(56) References Cited

U.S. PATENT DOCUMENTS

| 3,971,362 A | 7/1976 | Pope et al. |
| 4,278,077 A | 7/1981 | Mizumoto |

(Continued)

FOREIGN PATENT DOCUMENTS

| DE | 34 40 177 | 5/1986 |
| EP | 1 715 697 | 10/2006 |

(Continued)

OTHER PUBLICATIONS

Electronic Endoscope.
(Continued)

*Primary Examiner* — Anhtuan T Nguyen
*Assistant Examiner* — Alexandra Newton
(74) *Attorney, Agent, or Firm* — Pearl Cohen Zedek Latzer Baratz LLP

(57) ABSTRACT

An in-vivo imaging device and method for performing spectral analysis include inserting the in-vivo device into a patient's lumen, illuminating the tissue lumen and collecting the light scattered and reflected from the tissue. The device may comprise at least six illumination sources for illuminating the tissue. At least two of the six illumination sources illuminate at a different wavelength in the blue spectral region, at least two illuminate at a different wavelength in the green spectral region, and at least two illuminate at a different wavelength in the red spectral region. The illumination sources are adapted to illuminate in groups of three, wherein each group of three illumination sources comprises one illumination source that illuminates in the blue spectral region, one in the green spectral region, and one in the red spectral region. Each group of three illumination sources illuminates simultaneously.

4 Claims, 10 Drawing Sheets

(51) Int. Cl.
*A61B 1/00* (2006.01)
*A61B 1/06* (2006.01)

(56) References Cited

U.S. PATENT DOCUMENTS

| | | | |
|---|---|---|---|
| 4,668,860 | A | 5/1987 | Anthon |
| 4,689,621 | A | 8/1987 | Kleinberg |
| 4,844,076 | A | 7/1989 | Lesho et al. |
| 4,936,823 | A | 6/1990 | Colvin et al. |
| 5,241,170 | A | 8/1993 | Field et al. |
| 5,279,607 | A | 1/1994 | Schentag et al. |
| 5,604,531 | A | 2/1997 | Iddan et al. |
| 5,646,781 | A | 7/1997 | Johnson, Jr. |
| 5,697,384 | A | 12/1997 | Miyawaki et al. |
| 5,812,187 | A | 9/1998 | Watanabe |
| 5,819,736 | A | 10/1998 | Avny et al. |
| 5,908,294 | A | 6/1999 | Schick et al. |
| 5,929,901 | A | 7/1999 | Adair et al. |
| 5,993,378 | A | 11/1999 | Lemelson |
| 6,088,606 | A | 7/2000 | Ignotz et al. |
| 6,240,312 | B1 | 5/2001 | Alfano et al. |
| 6,449,006 | B1 | 9/2002 | Shipp |
| 7,477,931 | B2 | 1/2009 | Hoyt |
| 2001/0035902 | A1* | 11/2001 | Iddan et al. ............ 348/76 |
| 2001/0051766 | A1 | 12/2001 | Gazdzinski |
| 2002/0054290 | A1 | 5/2002 | Vurens et al. |
| 2002/0103417 | A1 | 8/2002 | Gazdzinski |
| 2002/0171669 | A1 | 11/2002 | Meron et al. |
| 2002/0193664 | A1 | 12/2002 | Ross et al. |
| 2002/0198439 | A1 | 12/2002 | Mizuno |
| 2003/0167000 | A1 | 9/2003 | Mullick et al. |
| 2003/0174208 | A1 | 9/2003 | Glukhovsky et al. |
| 2003/0208107 | A1 | 11/2003 | Refael |
| 2004/0111031 | A1 | 6/2004 | Alfano et al. |
| 2005/0124858 | A1 | 6/2005 | Matsuzawa et al. |
| 2005/0148842 | A1 | 7/2005 | Wang et al. |
| 2005/0154277 | A1 | 7/2005 | Tang et al. |
| 2006/0036131 | A1 | 2/2006 | Glukhovsky |
| 2009/0059207 | A1 | 3/2009 | Nerin et al. |
| 2009/0097725 | A1 | 4/2009 | Krupnik et al. |
| 2010/0277570 | A1 | 11/2010 | Komiya et al. |

FOREIGN PATENT DOCUMENTS

| | | |
|---|---|---|
| JP | 57-45833 | 3/1982 |
| JP | 4109927 | 4/1992 |
| JP | 1992-14453 | 5/1992 |
| JP | 5015515 | 1/1993 |
| JP | 2001224553 | 8/2001 |
| JP | 2006068488 | 3/2006 |
| JP | 2006184033 | 7/2006 |
| JP | 2009131324 | 6/2009 |
| JP | 2010075513 | 4/2010 |
| JP | 2010227200 | 10/2010 |
| WO | WO 01/08548 | 2/2001 |
| WO | WO 01/50941 | 7/2001 |
| WO | WO 01/65995 | 9/2001 |
| WO | WO 2004/012461 | 2/2004 |
| WO | WO 2008/105370 | 9/2008 |
| WO | WO 2010/086859 | 8/2010 |

OTHER PUBLICATIONS

Malavika Chandra et al; Spectral areas and ratios classifier algorithm for pancreatic tissue classification using optical spectroscopy, Jouranal of Biomedical Optics; Jan. / Feb. 2010; vol. 15(1) 010514-1-010514-3.

Myers D, McGraw M, George M, Mulier K, Beilman G.; Tissue hemoglobin index: a non-invasive optical measure of total tissue hemoglobin, BioMeasurement Division, Hutchinson Technology Inc, 40 West Highland Park Drive NE, Hutchinson, MN 55350-9784, USA. dean.myers@hti.htch.com.

International Search Report of Application No. PCT/IL2011/050014 dated Apr. 20, 2012.

English Translation of Office Action of Chinese Application No. 201180055032.6 issued on Jan. 22, 2015.

English Translation of Office Action of Japanese Application No. 2013-539399 mailed on Jul. 7, 2015.

Supplementary Search Report of Application No. EP 11 84 2069 mailed on Aug. 9, 2013.

"Robots for the future"—Shin-ichi, et al., printed Nov. 29, 2001.

"The Radio Pill, Rowlands", et al., British Communications and Electronics, Aug. 1960, pp. 598-601.

"Video Camera to "Take""—RF System lab, Dec. 25, 2001.

"Wellesley company sends body montiors into space"—Crum, Apr. 1998.

www.rfnorkia.com—NORIKA3, Jan. 1, 2002.

"Wireless transmission of a color television moving image from the stomach using a miniature CCD camera, light source and microwave transmitter", Swain CP, Gong F, Mills TN. Gastrointest Endosc 1997;45:AB40.

BBC News Online—Pill camera to 'broadcast from the gut', Feb. 21, 2000, www.news.bbc.co.uk.

Deep subsurface imaging in tissues using spectral and polarization filtering. S.G Demos. Jul. 3, 2000/vol. 7, No. 1. Optics Express.

* cited by examiner

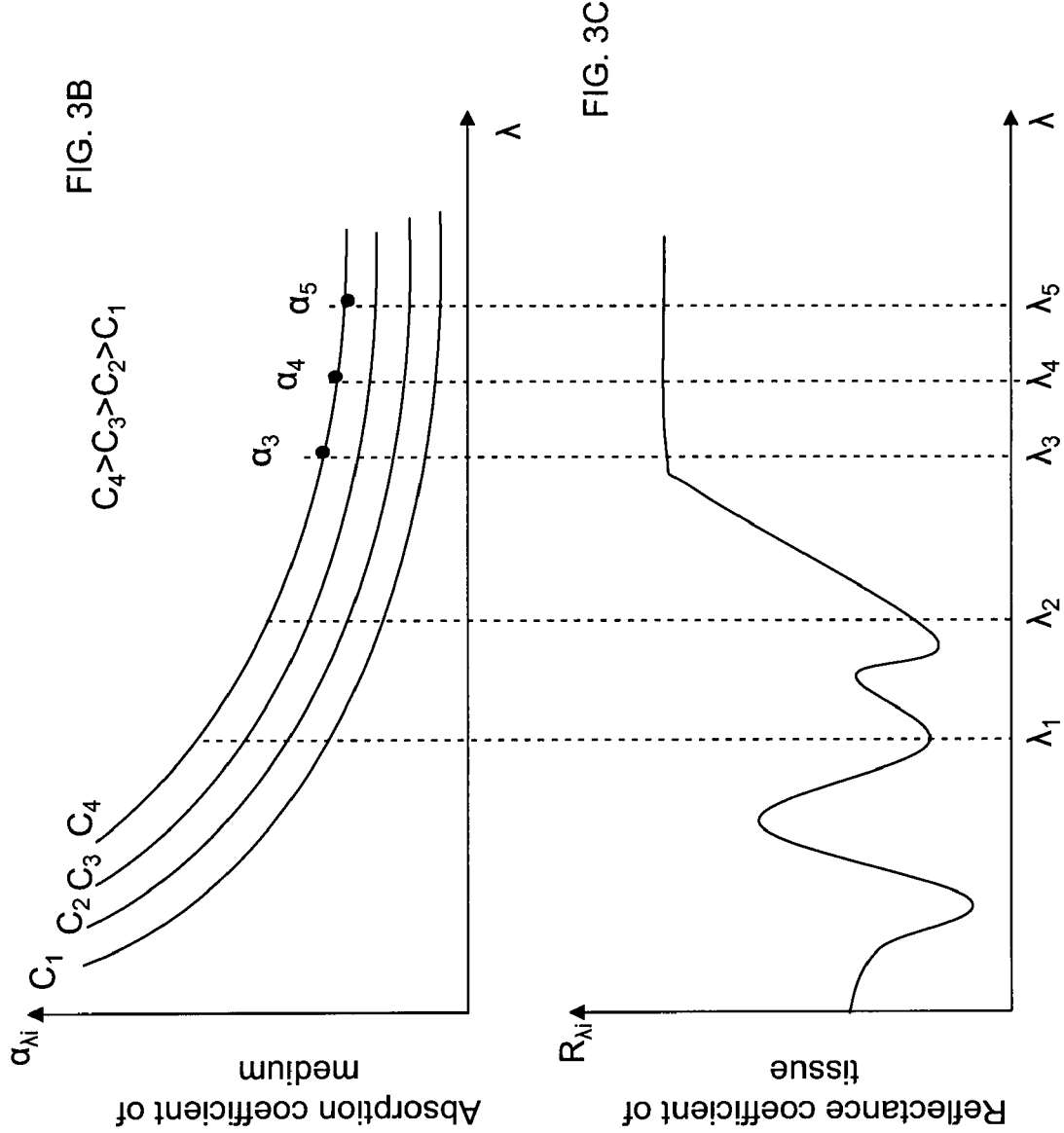

IN-VIVO IMAGING DEVICE AND METHOD FOR PERFORMING SPECTRAL ANALYSIS

CROSS-REFERENCE TO RELATED APPLICATIONS

This application is a National Phase Application of PCT International Application No. PCT/IL2011/050014, International Filing Date Nov. 16, 2011, entitled "In-Vivo Imaging Device and Method for Performing Spectral Analysis" published on May. 24, 2012 as International Publication No. WO 2012/066553, claiming priority of U.S. Provisional Patent Application No. 61/414,060, filed Nov. 16, 2010, which is incorporated herein by reference in its entirety.

FIELD OF THE INVENTION

The present invention is related to the field of in vivo imaging, and more specifically to in-vivo imaging devices that perform spectral analysis.

BACKGROUND OF THE INVENTION

Detection of lesions, e.g. along the gastrointestinal (GI) tract is usually done by an endoscope. An endoscope acquires images of the GI tract while it is being pushed along the GI tract, and thus the GI lumen is being scanned for any abnormality, for example, polyps. However, detection of the presence of lesions is not enough. There is also the need to analyze the lesion and determine whether a lesion is cancerous or benign. Changes in cell structure (e.g. size of nucleus and density of cells) and changes in blood content, which are typical to cancer, pre-cancer and other bowel diseases can be discovered and analyzed by spectral means.

A few probes, which perform elastic scattering spectroscopy, are known. These probes may determine by the characteristics of light scattering off the tissue, the type of the lesion, e.g. whether cancerous or benign. However, these probes are all inserted through the patient's mouth, which might cause some discomfort for the patient during insertion of the probe and during its manipulation within the lumen. In addition, these probes that provide elastic scattering data do not provide a "white light" or color image of the lumen, which may be needed in order to locate the position of the lesion along the GI tract.

Therefore, there is a need for an improved in vivo device that can provide both spectral information along with standard images of the in-vivo lumen, and thus a more accurate determination of the severity of the pathology may be carried out as well as a determination of the pathology location.

SUMMARY OF THE INVENTION

The present invention provides devices and methods of performing spectral analysis, along with providing in-vivo images of the lumen they are inserted to.

In one embodiment of the present invention, an in-vivo imaging device performing spectral analysis may comprise a plurality of different illumination sources. In some embodiments, the in-vivo device may comprise an imager, which may comprise standard RGB filters, such that illuminating in an alternating mode is done by operating each of the plurality of illumination sources during a different time period. In other embodiments, the imager may comprise Color Enhancement filter types or Color Separation filter types disposed thereon. The color filters may be adapted to prevent overlap between illumination in the blue, green and red spectral regions collected by the imager. In such embodiments, the plurality of illumination sources (e.g. at least six illumination sources, each illuminating at a different wavelength) may illuminate in groups of illumination sources. Each group may consist of one illumination source that illuminates in a wavelength corresponding to the blue region of the spectrum, one illumination source that illuminates in a wavelength corresponding to the green region of the spectrum, and one illumination source that illuminates in a wavelength corresponding to the red region of the spectrum. Every group that includes three different illumination sources as such, may illuminate simultaneously, thus shortening the illumination period as well as the light collection period.

In some embodiments, the in-vivo device may be a swallowable autonomous device, whereas in other embodiments the device may be an endoscope or any other device or probe.

In some embodiments, a method for performing spectral analysis may comprise inserting into a patient's lumen an in-vivo imaging device that may comprise a plurality of illumination sources, where each illumination source may illuminate at a different wavelength. In some embodiments, the method may comprise illuminating the patient's tissue in an alternating mode.

In some embodiments, the method may further comprise collecting light that is reflected off the tissue lumen. This may be done by an imager contained within the device. In some embodiments, the method may comprise the step of analyzing the reflected light, and the step of determining location of a pathology as well as determining characteristics of the pathology. In some embodiments, the step of analyzing the reflected light may comprise creating a color image. By observing the color image, one may determine presence of a pathology and may further determine its location along the lumen. Furthermore, characteristics of the pathology, e.g. its blood concentration, may also be inferred from the color image, for example, by examining its grayness levels at the different image areas; the imaged lesion area and its imaged surroundings.

In some embodiments, the step of analyzing the scattered and reflected light may be performed by either an analyzing unit or by an operator of the in-vivo device. An analyzing unit may be part of the in-vivo device, or may be located externally to it.

In one embodiment of the invention, an in-vivo imaging device performing spectral analysis may comprise a spherical window. The device may further comprise at least four illumination sources for illuminating a tissue at different wavelengths, and an image sensor. In some embodiments, the device may comprise optical means for directing light emitted from the at least four illumination sources onto a reflector adapted to redirect light beams from the illumination sources onto the tissue. An example of such a reflector may be a cone mirror. The reflector, e.g. a cone mirror, may be configured to project the directed light onto the tissue at an angle substantially parallel to the field of view angle of the device. In some embodiments the reflector, e.g. cone mirror, may be located in the center of the spherical window in order to avoid stray light. In some embodiments, the device may further comprise an optical system for focusing light scattered and reflected off the tissue onto the image sensor. In some embodiments, the at least four illumination sources, the image sensor, the reflector and the optical system may be positioned behind the concave side of the spherical window and may operate there through.

In some embodiments, the field of illumination may be substantially the same as the field of view, i.e. the angle of illumination may be substantially parallel to the field of view angle.

In some embodiments, the optical means within the device may comprise a collimating lens for causing the light emitted from the at least four illumination sources to emerge in a parallel light beam. The device may further comprise a folding mirror for redirecting the parallel light beam towards a condensing lens, such that the condensing lens is for condensing the light beam and directing it towards the cone mirror.

According to some embodiments, at least two of the at least four illumination sources may illuminate in wavelengths that are suitable for determining presence of blood in the tissue, and the other two illumination sources may illuminate in wavelengths that are suitable for determining presence of bile or other intestinal content. In some embodiments, the wavelengths suitable for determining presence of blood may be selected from the range of 400-600 nm, and the wavelengths for determining presence of bile or other intestinal content may be selected from the range of 600-900 nm.

In some embodiments, an in-vivo imaging device performing spectral analysis may comprise a spherical window. The device may further comprise an illumination unit for illuminating a tissue at different wavelengths. In some embodiments, the illumination unit may be located in the center of the spherical window. In some embodiments, the he device may further comprise an image sensor, and an optical system for focusing light scattered and reflected off the tissue onto the image sensor. In some embodiments, the illumination unit, the image sensor, and the optical system may be positioned behind the spherical window.

In some embodiments, the illumination unit may comprise at least four illumination sources for illuminating the tissue at different wavelengths.

According to other embodiments, an in-vivo imaging device performing spectral analysis may comprise a first illumination source for illuminating a tissue, an image sensor, and an optical system for focusing light reflected off the tissue onto the image sensor. In some embodiments, the device may further comprise a mini-spectrometer positioned in close proximity to a second illumination source for collecting scattered light. In some embodiments, the mini-spectrometer may comprise a grating to separate light scattered from the tissue into separated specific wavelengths, and a detector for collecting the separated scattered light.

In some embodiments, the mini-spectrometer may comprise a plurality of pixels arranged as a vector detector. In other embodiments, the mini-spectrometer may comprise a plurality of pixels arranged as a matrix detector.

In some embodiments, the device may comprise a cylindrical focusing lens for receiving the separated scattered light after being separated by the grating, and for focusing each of the separated specific wavelengths onto a different specific pixel of the plurality of pixels that form the mini-spectrometer.

In some embodiments, a method for performing spectral analysis may comprise the step of inserting into a patient's lumen an in-vivo imaging device similar to the device comprising a cone mirror. The method may further comprise the step of illuminating the patient's tissue lumen by projecting light off the cone mirror. In some embodiments, the method may comprise collecting light that is reflected and scattered off the tissue lumen. The method may further comprise analyzing the reflected and scattered light, and determining location of a pathology as well as pathology characteristics. In some embodiments, the analyzing step may comprise acquiring a color image, according to which the location of a pathology along the lumen may be determined, whereas the characteristics of the pathology may be determined by analysis of the scattered light (e.g. analysis of the various wavelengths of the scattered light).

In other embodiments, a method for performing spectral analysis may comprise the step of inserting into a patient's lumen an in-vivo imaging device similar to the device comprising a mini-spectrometer. The method may further comprise illuminating the patient's tissue lumen, and collecting light that is reflected off the tissue lumen by an image sensor. In some embodiments, the method may comprise collecting light that is scattered off the tissue lumen by the mini-spectrometer. The method may further comprise the steps of analyzing the reflected and scattered light, and the step of determining location of a pathology along the lumen, as well as determining pathology characteristics.

BRIEF DESCRIPTION OF THE DRAWINGS

The above and other objects and advantages of the invention will be apparent upon consideration of the following detailed description, taken in conjunction with the accompanying drawings, in which the reference characters refer to like parts throughout and in which:

FIGS. 3A-3C illustrate a schematic system for performing spectral analysis, a schematic graph of medium absorption vs. wavelength, and a schematic graph of tissue reflectance vs. wavelength, respectively, in accordance with an embodiment of the present invention;

Figure 1:
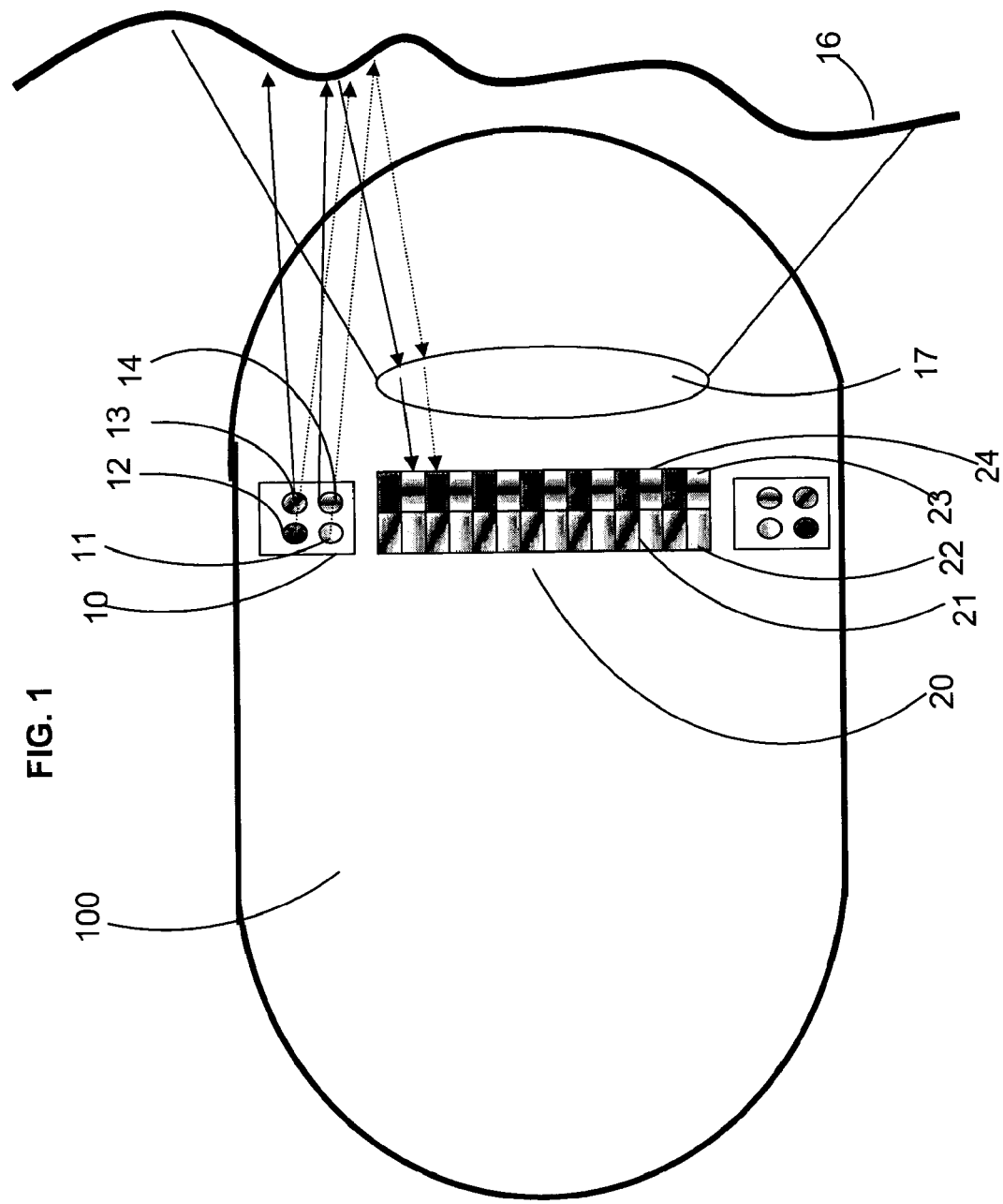
FIG. 1 illustrates a schematic lengthwise sectional view of an in-vivo imaging device in accordance with one embodiment of the present invention.

It will be appreciated that for simplicity and clarity of illustration, elements shown in the figures have not necessarily been drawn to scale. For example, the dimensions of some elements may be exaggerated relative to other elements for clarity. Further, where considered appropriate, reference numerals may be repeated among the figures to indicate corresponding or analogous elements.

DETAILED DESCRIPTION OF THE DRAWINGS

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The in-vivo imaging devices described below are a modification of the current elastic scattering detecting devices as known today. The in-vivo devices described in the present invention may provide images of an illuminated tissue, as well as spectral analysis information on the illuminated tissue, which may enable a physician to provide a more accurate and complete analysis of the patient's condition. The physician receives information related to the location of the lesion along the lumen, e.g. at which organ along the GI is the lesion located (which may be determined from the color images that may be acquired by the in-vivo devices described in the present invention as well as information on the lesion's diagnostics (which may be determined by the spectral information acquired by the in-vivo devices of the present invention). In addition, in-vivo devices described in the present invention may be swallowable, autonomous, wireless devices, which may be inserted to the patient more easily than current elastic scattering detecting devices as known today. However, the present invention is not limited to swallowable autonomous devices and may be directed to other devices, such as endoscopes or other probes.

Reference is now made to FIG. 1, which illustrates a schematic lengthwise sectional view of an in-vivo imaging device in accordance with one embodiment of the present invention. According to embodiments of the present invention, as illustrated in FIG. 1, in-vivo imaging device 100 may be a swallowable, autonomous device that includes no wired connection to an external device. The in-vivo imaging device 100 may be self-powered and may transmit collected information to an external receiver, through wireless transmission. In-vivo device 100 may be capsule shaped or spherical shaped, though other shapes may be used as long as they enable easy insertion and passage of device 100 throughout in-vivo lumens, e.g. the GI tract.

According to embodiments of the present invention, in-vivo device 100 may comprise a plurality of illumination units 10 in order to illuminate the lumen wall, e.g. lumen wall 16, as device 100 moves along the lumen. In some embodiments, illumination unit 10 may comprise a matrix of at least four illumination sources, e.g. illumination sources 11, 12, 13 and 14. In some embodiments, there may be more than one illumination unit 10 positioned beside an image sensor 20, e.g. there may be four illumination units 10 positioned around imager 20. Other numbers of illumination sources per illumination unit may be used. The advantage of the light source configuration of device 100, such that there is more than one illumination unit matrix 10 located in circular symmetry with respect to optical system 17, is that the different illumination sources 11, 12, 13, 14 (and/or others) may distribute the light relatively evenly to achieve relatively uniform light distribution in the field of view of the optical imaging system 17.

In some embodiments, illumination sources, such as those designated as 11 and 12 may illuminate in wavelengths that are suitable for determining presence of blood in the tissue. For example, illumination source 11 and illumination source 12 may illuminate in any wavelength selected from 415 nm, 540 nm, 560 nm, 570 nm, and 600 nm, as these are examples of wavelengths which experience good absorbance in blood, specifically in hemoglobin. Other wavelengths that experience good absorbance in blood may be used. Other numbers of illumination sources that illuminate in wavelengths suitable for blood detection, may be used. Examples of LEDs that illuminate at a specific center wavelength, which experiences good absorbance in hemoglobin, may be KPHK-1608MBC manufactured by Kingbright that illuminates at 430 nm, NESB007A by Nichia that illuminates at 470 nm, LTL29S by Osram that illuminates at 523 nm, SM0603PGC by Bivar that illuminates at 555 nm, TLPGE1008A by Toshiba (EBV) that illuminates at 562 nm, TLGE1008A by Toshiba (EBV) or KPHHS-1005CGCK by Kingbright that illuminates at 674 nm, and HSMD-C190 by Avago (Farnell) that illuminates at 605 nm. Other LEDs may be used, or any other suitable sources.

In some embodiments, illumination sources such as 13 and 14 may illuminate in wavelengths that are suitable for detection of bile or other intestinal content. For example, illumination source 13 may illuminate in a wavelength of 700 nm, and illumination source 14 may illuminate in a wavelength of 850 nm. In some embodiments, illumination sources 13 and 14 may illuminate in any wavelength selected from wavelength range of 600 nm to 900 nm, as this is a range of wavelengths which experience good absorbance in bile (whereas these wavelengths experience substantially no absorbance in hemoglobin). Other wavelengths that experience good absorbance in bile or other intestinal content may be used. Other numbers of illumination sources that illuminate in wavelengths suitable for detection of bile or other intestinal content, may be used. Examples of LEDs that illuminate at a specific center wavelength, which experiences good absorbance in intestinal content, may be KPHHS-1005SECK by Kingbright that illuminates at 610 nm, HSMS-C190 by Avago (Farnell) that illuminates at 630 nm, SM0603URC by Bivar that illuminates at 660 nm, KP1608SF4C by Kingbright that illuminates at 880 nm, and SMT610, SMT700, and SMT820 by Epitex that illuminate at 610 nm, 700 nm, and 820 nm, respectively. Other LEDs may be used or any other suitable sources.

In order to determine whether the reflected light indicates on presence of blood and not of other lumen content, such as bile (which happens to have a similar transmission spectra to the transmission spectra of blood), there is a need to compare the reflected light to transmission spectra of blood and to transmission spectra of bile. Methods of determining whether blood, bile or both are present in-vivo are described in International Publication Application Number WO 2010/086859 entitled "DEVICE, SYSTEM AND METHOD FOR DETECTION OF BLEEDING", of the common assignee of the present invention, which is incorporated herein by reference in its entirety. For example, according to the description of FIG. 11 of WO 2010/086859, a "blood score" and a "bile score" are calculated in order to differentiate between the presence of blood in-vivo and the presence of bile. The "blood score" may be calculated from at least two readings measuring light intensity in at least two different wavelengths selected from the range of 400-600 nm (which are the wavelengths at which blood absorbs light with high specificity), whereas the "bile score" may be calculated from at least two readings detecting light intensity at at least two different wavelengths selected from the range of 600-900 nm (which are the wavelengths at which bile absorbs light at high specificity). A processor may compare between the measured transmission spectra ("blood score" and "bile score") with corresponding reference spectra and may determine the concentration of either bile, blood or both.

In other embodiments, instead of illumination unit 10 comprising a group of illumination sources as described above, illumination sources 11, 12, 13, and 14 may be positioned apart from one another, and not within a matrix of illumination sources. In some embodiments, at least one of each illumination sources 11, 12, 13, 14 (and/or others) that are not within a matrix but positioned apart from one another, may be located around imager 20, symmetrically with respect to the optical system 17.

According to some embodiments, imager 20 may comprise a "standard" RGB imager, e.g. imager 20 may be a CMOS or CCD image sensor comprising a Bayer filter arrangement. In order to collect reflected light and later create a color image that would assist in determining presence and severity of a polyp in-vivo, a few methods of illumination and light collection may be possible. One method may be illuminating in alternating mode, e.g. illuminating with different illumination sources at different time periods. For example, illumination source 11 may illuminate alone for a certain predetermined period, and illumination source 12 may illuminate thereafter for the same or for a different predetermined time period. Only then may illumination source 13 illuminate for a predetermined period, and illumination source 14 may then follow to illuminate for another period of time. In embodiments where there is more than one illumination source of the same wavelength (whether it is any of illumination sources 11, 12, 13, 14, or others), each of the illumination sources of the same wavelength illuminates simultaneously, followed by the next type of illumination source, which is of a different wavelength. By using this mode of alternating the illumination sources, the imager need not require any special filters, and a combined image of all reflected light at all wavelengths is later created by a processor (not shown), which may be either located within the device 100 or external to the device 100.

In other embodiments, other methods of illumination and collection of light may be used. For example, imager 20 may comprise several filters that correspond to the illumination sources' wavelengths. Such filters may be narrow band filters, interference filters or diffractive optical element (DOE) filters. As shown in FIG. 1, imager 20 may comprise filters at pixel scale, e.g. filters 21, 22, 23, and 24, which correspond to illumination sources 11, 12, 13, and 14, respectively. That is, different pixels of imager 20 have different color sensitivity that corresponds to the wavelengths which light is illuminated at. In some embodiments, since imager 20 comprises filters dedicated to collect light at different specific wavelengths, which correspond to the wavelengths which light is illuminated at, there is no need for illuminating in an alternating mode, but rather all illumination sources may illuminate simultaneously. A color image may be created from the light collection done by imager 20, and thus presence and diagnostics of lesions may be inferred.

In some embodiments, imager 20 (FIG. 1) may comprise long pass, short pass, wide band pass filters or a combination thereof, for each of the blue, green and red spectrums. For example, imager 20 may comprise several filters in front of it; filter 1, filter 2 and filter 3 (not shown), that may be used. Filter 1 may be used for filtering the blue spectra according to the light-pass curve denoted Filter 1, filter 2 may be used for filtering the green spectra according to the light-pass curve denoted Filter 2, and filter 3 may be used for filtering the red spectra according to the light-pass curve denoted Filter 3. In some embodiments, filter 1 and filter 3 may be wide band pass filters as is filter 2, while in other embodiments filter 1 may be a short pass filter and filter 3 may be a long pass filter. Examples of long pass filters in large scale that may be implemented in pixel scale (e.g. Filter 3) may be LPF-600, LPF-650, LPF-700, which are manufactured by CVI Melles Griot, Albuquerque, N.M. Examples of short pass filters in large scale that may be implemented in pixel scale (e.g. Filter 1) may be SPF-400, SPF-450, SPF-500, which are manufactured by CVI Melles Griot, Albuquerque, N.M. Examples of wide band pass filters in large scale that may be implemented in pixel scale (e.g. Filter 2) may be F40-550.0-4, F70-550.0-4, which are manufactured by CVI Melles Griot, Albuquerque, N.M. Other examples for each of the long pass, short pass and wide band pass filters may be used.

Figure 2:
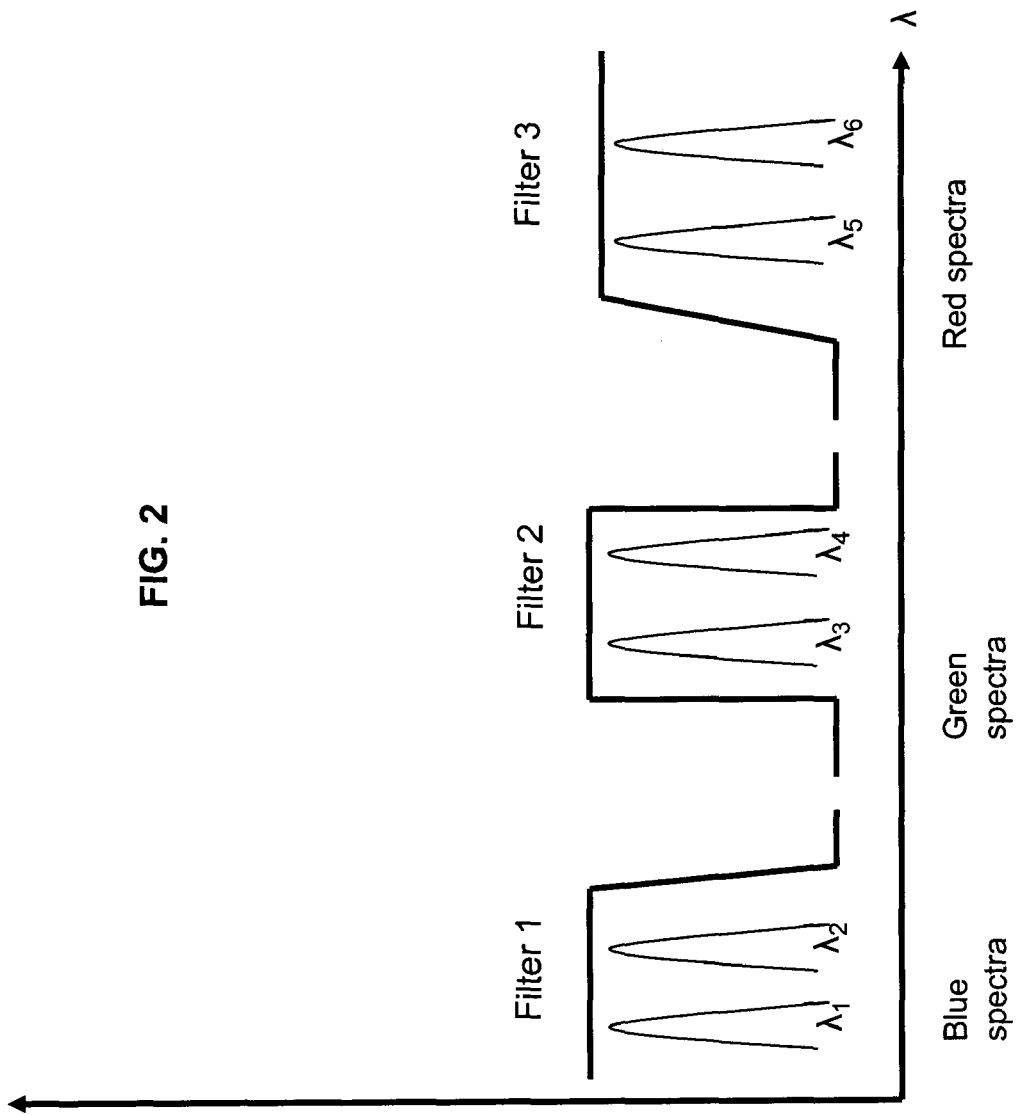
FIG. 2 illustrates a schematic graph of an illumination and light collection scheme in accordance with an embodiment of the present invention.

Reference is now made to FIG. 2, which illustrates a schematic graph of an illumination and light collection scheme on a wavelength-intensity graph, in accordance with an embodiment of the present invention. According to some embodiments, another method of image acquisition may be practiced, which is a compromise between illuminating in alternating mode, where each illumination source illuminates at a different time period, and between using complex filters placed on the image sensor. This compromise is suitable for use in in-vivo devices that passively move along in-vivo lumens, e.g. along the GI tract, and which are not maneuverable, such as autonomous swallowable capsules. When using a relatively large number of illumination sources and illuminating each illumination source at a different and separate time period, the illuminating process might be time consuming such that the images acquired for each illuminating period might not be the same, since the device has already moved to a new location along the lumen. This might cause difficulties in later creating the color images. On the other hand, adding complex filters on the image sensor might be expensive, even assuming that such filters are indeed available. Therefore, the following method of illumination and light collection may be easily implemented in in-vivo devices as described in the present invention, and combines the advantages of both of the previously mentioned methods.

In some embodiments, the illumination scheme may be such that illumination sources of specific center wavelengths having illumination scheme depicted by the curves $\lambda_1$, $\lambda_2$, $\lambda_3$, $\lambda_4$, $\lambda_5$, and $\lambda_6$, may illuminate in an alternating mode, but alternating between groups of illumination sources. For example, a first group of illumination sources each having a specific center wavelength, which may illuminate simultaneously, may comprise one of a plurality of illumination sources that illuminate in the blue spectral region, e.g. $\lambda_1$, one of a plurality of illumination sources that illuminate in the green spectral region, e.g. $\lambda_3$, and one of a plurality of illumination sources that illuminate in the red spectral region, e.g. $\lambda_5$. All of the three illumination sources: $\lambda_1$, $\lambda_3$, and $\lambda_5$ may illuminate simultaneously during a first time period, since there is substantially no overlap between the filters of imager 20 along the wavelength axis, neither is there an overlap between the wavelengths of the illumination sources $\lambda_1$, $\lambda_3$, and $\lambda_5$. In some embodiments, subsequent to the first illumination period, there may be a second illumination period during which a second group of narrow band illumination sources may illuminate simultaneously. For example, during the second illumination period, one of a plurality of illumination sources that illuminate in the blue spectral region, e.g. $\lambda_2$, which may illuminate at a different wavelength than $\lambda_1$, may simultaneously illuminate with one of a plurality of illumination sources that illuminates in the green spectral region, e.g. $\lambda_4$ (which may illuminate at a different wavelength than $\lambda_3$), and simultaneously illuminate with one of a plurality of illumination sources that illuminates in the red spectral region, e.g. $\lambda_6$ (which may illuminate at a different wavelength than $\lambda_5$). Yet again, there is substantially no overlap between the filters of imager 20, neither is there overlap between the wavelengths of the illumination sources $\lambda_2$, $\lambda_4$, and $\lambda_6$. Other numbers of groups of illumination sources may be used.

The image sensor 20 may collect light reflected from a tissue or fluid being in the field of view of imaging device 100 (FIG. 1) in the three spectrums at the same time period, or cycle, for every group of three (or more) different illumination sources. Therefore, the total illumination time period of the illumination groups altogether, e.g. of the two groups disclosed above, may be shorter than the total illumination period of when illuminating with every illumination source for a different and separate time period. Shorter total illumination period may enable collection of reflected light that correspond to each spectrum, at substantially the same in-vivo location. Illuminating and collecting reflected light within a short period of time (e.g. between 2 ms to 4 ms) may ensure the reflected light is reflected from substantially the same in-vivo location, before the device has moved onto another in-vivo location. A combined image of all the spectra, which may be created by a processor (not shown), may be similar to a white light image.

In some embodiments, instead of adding pixel scale filters onto image sensor 20 (FIG. 1), other large scale filters that may be disposed on the entire image sensor 20 may be used. Since a standard RGB imager (e.g. Bayer filter arrangement) comprises filters that enable overlap between blue, green and red spectral regions, additional filters that may be adapted to prevent the overlap between illumination in blue, green and red spectral regions collected by the imager may be disposed on imager 20. These filters that may be disposed on the image sensor 20 allow transmission of three bands of pure color, e.g. blue, green, and red, while blocking intermediate wavelengths. Thus, light collection may be done for each of the illumination sources having a specific center wavelength alone, without a crossover between spectrums. Light collection may be done for each of the illumination sources' spectrums alone and thus in addition to the ability of creating a color image of the lumen, each of the specific collected spectrums may be used to indicate on tissue characteristics (e.g. presence of blood). Examples for such large scale filters that may be placed onto the imager 20 may be SPECTRA-$^{PLUS}$ XB29 by Omega Optical Incorporated, V30 by Hoya, ZX000019 by IRIDIAN, or FF01-464/542/639-25 by Semrock, all of which are Color Enhancement filter types or Color Separation filter types. Other large scale filters that substantially prevent the overlapping regions between blue/green and green/red spectrums may be used.

In such embodiments, when such color enhancement filters are placed over imager 20, illumination sources of specific center wavelengths having, for example, illumination scheme depicted by the curves $\lambda_1$, $\lambda_2$, $\lambda_3$, $\lambda_4$, $\lambda_5$, and $\lambda_6$ (FIG. 2), may illuminate in an alternating mode. The alternating mode of illumination may comprise simultaneous illumination of a group of illumination sources, each selected from a different spectrum; blue, green or red. For example, a first group of illumination sources that may illuminate simultaneously may be $\lambda_1$, $\lambda_3$, and $\lambda_5$, while a second group of illumination sources that may illuminate simultaneously may be $\lambda_2$, $\lambda_4$ and $\lambda_6$. Since illumination is done in groups of illumination sources illuminating at once, the total illumination period of all the groups altogether (e.g. between 2 ms to 4 ms) may be relatively shorter than the total illumination period of when illuminating with each illumination source for a different time period subsequent to an illumination period of a different illumination source. As described with regards to FIG. 2, illuminating and collecting reflected light within a short period of time (e.g. 2 ms-4 ms) may ensure the reflected light is reflected from substantially the same in-vivo location. In some embodiments, device 100 may comprise a transmitter (not shown), typically an RF transmitter. The image data or other data captured by the in-vivo device 100 may be transmitted as a data signal by wireless connection, e.g. by a wireless communication channel, by the transmitter via an antenna (not shown) located within the device. The data signal may be received by an external recorder or receiver (not shown).

According to some embodiments, once the image is created from the light reflections, the entire image is analyzed either by the operator, e.g. a physician, or by an analyzer, either inside the device 100 or external to it. The image may be analyzed for the detection of potential lesions and for detection of blood concentration. Once a captured surface is detected, having the appearance of a potential lesion, blood concentration may be calculated for the "lesion area" in the image and for its surroundings in that same image. One possible method of calculating blood concentration from the color image may be done by calculating the gray level, of the red areas in the image. If the calculated blood concentration at the "lesion area" is higher compared to the blood concentration in its surroundings, it may be concluded that it is a cancerous lesion. However, if the blood concentration in the "lesion area" is approximately the same as that in the surroundings, it may be concluded that the lesion is benign.

The following methods may be implemented on spectral information that may be collected by any device that comprises a plurality of illumination sources, each of the illumination sources having a different specific center wavelength (e.g. narrow band illumination). The following methods may, for example, be implemented on spectral information, (e.g. images created from reflections of light off a tissue) provided by in-vivo devices such as in-vivo device 100 (FIG. 1), in-vivo device 200 (FIG. 4, described later in detail), in-vivo device 300 (FIGS. 5A-5B, described later in detail) or in-vivo device 400 (FIGS. 6A-6B, described later in detail). Other devices that may provide spectral information (e.g. collected light reflections), for example, an endoscope or any other device or probe that comprises narrow band illumination sources, may be used. These methods of performing spectral analysis and thus determining blood concentration levels from the color image may be done by calculating light intensity that is collected by the image sensor contained within the device. Following calculations of the collected light intensity, reflection from the tissue per each illuminated wavelength may be extracted. The method may comprise comparing reflection from the tissue for the different illuminated wavelengths and determining whether the lesion is cancerous or benign.

Figure 3A:
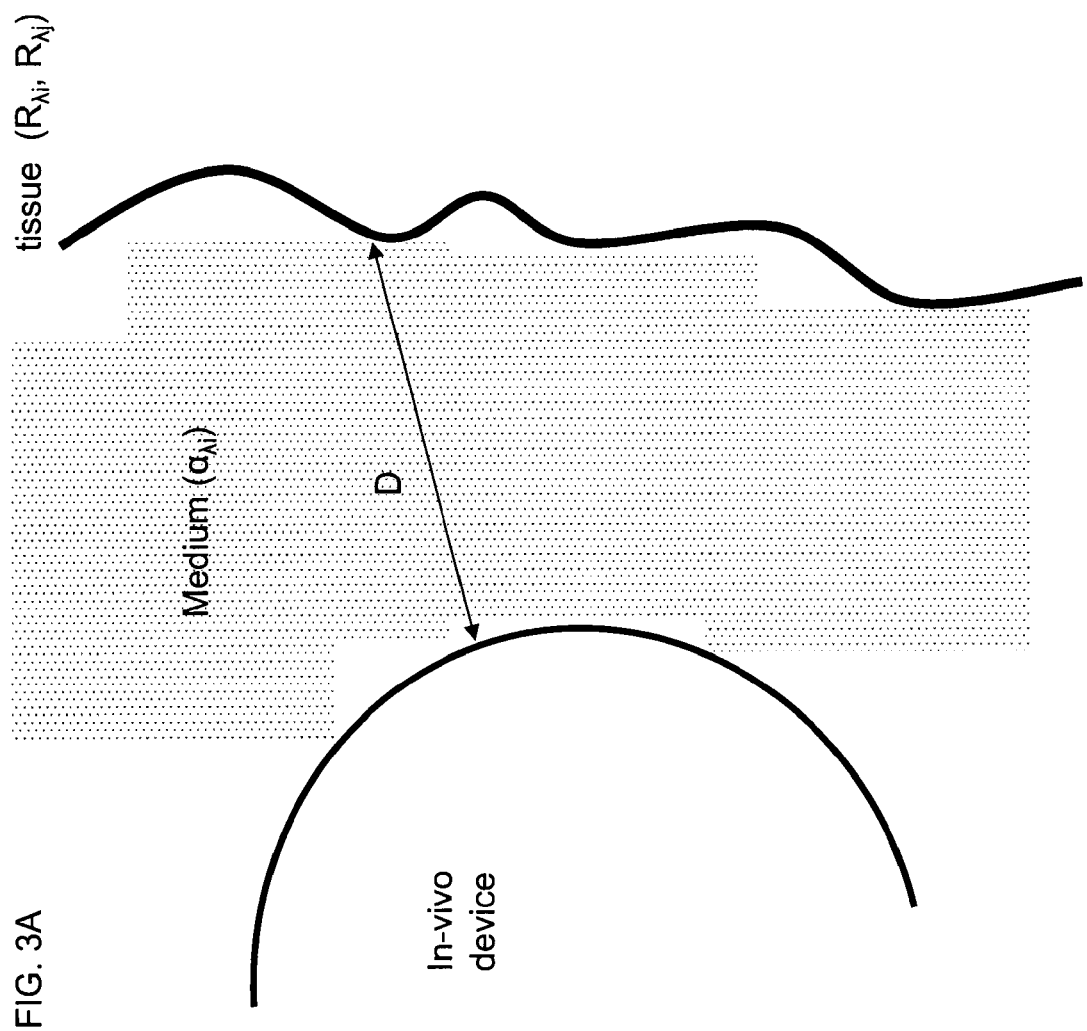

The governing equation for calculating the illumination intensity per illuminated wavelength may be defined as follows:

$$I_{\lambda_i} = \frac{I_{0_{\lambda_i}} \cdot A \cdot R_{\lambda_i}}{D^2} \cdot \exp(-2D \cdot C_{cont} \cdot \gamma_{\lambda_i} - 2D\beta) \quad \text{(i)}$$

wherein:

$I_{\lambda_i}$ is the intensity of light that is collected by the image sensor contained within the in-vivo device, following an illumination source illuminating at wavelength $\lambda_i$ ($I_{\lambda_i}$ depends on the optical design, e.g. on f number, and on the imager design, e.g. pixel size, in addition to depending on the illuminated wavelength. However, since the optical design and imager design are fixed and thereby unchanged for any wavelength illuminated by the same device, they may be neglected from the calculations);

$I_{0\lambda,i}$ is the illumination intensity of the illumination source, which may illuminate at wavelength $\lambda_i$;

A is the Albedo coefficient, which stands for the tissue reflectance as dependant on the angle of incidence (A has low correlation to wavelength);

$R_{\lambda,i}$ is the tissue reflectance, which depends on illuminated wavelength and tissue composition;

D is the distance between the in-vivo device and the tissue (FIG. 3A);

$C_{cont}$ is the concentration of the content or medium present between the device and the tissue;

$\gamma_{\lambda_i}$ is the absorbance coefficient of the content/medium at wavelength $\lambda_i$; and $\beta$ is the scattering coefficient of the content/medium, which has low correlation to illuminated wavelength.

For simplicity reasons, $C_{cont}$ and $\gamma_{\lambda_i}$ may be merged into one variable $\alpha_{\lambda,i}$, $\alpha_{\lambda,i}$ may represent the absorbance of the content/medium present between the device and the tissue $\alpha_{\lambda,i}$ is concentration dependent.

Therefore, equation (i) may be shortened into:

$$I_{\lambda_i} = \frac{I_{0\lambda,i} \cdot R_{\lambda_i} \cdot A}{D^2} \cdot e^{(-2D\cdot\alpha_{\lambda_i} - 2D\beta)} \quad \text{(ii)}$$

As mentioned above, comparing between reflections from the tissue caused by different illuminated wavelengths may provide indication on blood concentration. In some embodiments, it is assumed that the blood concentration of the tissue is proportional to the ratio between reflections from the tissue at different wavelengths. For example, blood concentration is proportional to:

$$\frac{R_{\lambda_3}}{R_{\lambda_1}} \text{ or to } \frac{R_{\lambda_3}}{R_{\lambda_2}},$$

wherein $R_{\lambda,i}$ is the reflection from the tissue at wavelength $\lambda_i$;

$\lambda_1$ and $\lambda_2$ are the wavelengths at which absorbance of hemoglobin is at a high level, close to or at its peak value; and $\lambda_3$ is a wavelength selected from a range of wavelengths at which absorbance of hemoglobin is very weak.

For example, $\lambda_1$ may be 540 nm, $\lambda_2$ may be 560 nm and $\lambda_3$ may be 610 nm or greater.

Another example of suitable wavelengths: $\lambda_1$ may be 576 nm, $\lambda_2$ may be 560 nm and $\lambda_3$ may be 610 nm or greater.

In some embodiments, it may be assumed that the device operates in a "clean" environment, that is, no content or medium is present between the device and the tissue, thus and $\beta$ may be neglected from equation (ii). Therefore, the ratios $$\frac{R_{\lambda_3}}{R_{\lambda_1}} \text{ and } \frac{R_{\lambda_3}}{R_{\lambda_2}}$$

may be extracted according to:

$$\frac{R_{\lambda_3}}{R_{\lambda_1}} = \frac{I_{\lambda_3}}{I_{\lambda_1}} \text{ and } \frac{R_{\lambda_3}}{R_{\lambda_2}} = \frac{I_{\lambda_3}}{I_{\lambda_2}} \quad \text{(iii)}$$

This calculation may be done to both the "lesion area" and to its surroundings, and then the two "real" blood concentrations may be compared in order to determine whether the lesion is cancerous or benign.

In other embodiments, in order to get more reliable results as to the accuracy of calculated blood concentration, there is a need to estimate the distance of the lesion from the imager, and the distance of its surroundings from the imager, and to estimate the absorption of the medium that surrounds the tissue and lesion, since in reality the environment is not a clean environment. Distance may be measured as described in FIG. 4 of US Patent Application Publication No. 2009/0097725, entitled "DEVICE, SYSTEM AND METHOD FOR ESTIMATING THE SIZE OF AN OBJECT IN A BODY LUMEN", of the common assignee of the present invention, which is incorporated herein by reference in its entirety. For example, distance of an object (e.g. polyp) may be calculated by a combination of laser spot distance and grayness level.

Absorption of the medium is wavelength dependent. There might be cases where a lesion that is distant from, for example, device 100 would absorb more light than a tissue closer to device 100, since the medium that surrounds the lesion absorbs well in the specific wavelength being illuminated. This might affect the distance measurement calculations, therefore, the affect of absorption of the medium surrounding the lesion needs to be normalized, such that indication of pathology would not depend on medium absorption ($\alpha_\lambda$ [measured in reciprocal mm]), but rather on tissue or lesion absorption.

For example, the illumination source intensity may be $I_0$. The illumination source may illuminate tissue located at a short distance $D_1$ with intensity $I_1$, while it may illuminate tissue located at a longer distance $D_2$ with intensity $I_2$. Since tissue reflectance ($R_{\lambda,i}$), which depends on illuminated wavelength and tissue composition, is unknown at any tissue location, reflectance from two known tissue locations (e.g. $D_1$ and $D_2$ are known) should be calculated. Calculations are done according to the following equations (wherein $\beta$ represents the scattering coefficient):

$$I_1 = \frac{I_0 \cdot R_1}{(D_1)^2} \cdot e^{(-2\alpha_\lambda \cdot D_1 - 2\beta \cdot D_1)} \quad \text{(iv)}$$

$$I_2 = \frac{I_0 \cdot R_2}{(D_2)^2} \cdot e^{(-2\alpha_\lambda \cdot D_2 - 2\beta \cdot D_2)} \quad \text{(v)}$$

Calculations may be done per each wavelength, for the two distances D1 and D2, and the absorption coefficient $\beta_\lambda$ may then be extracted and deducted so that indication of presence of a polyp would depend on polyp absorption alone, since the effect of medium absorption is eliminated.

In some embodiments, other calculations may be done in order to determine the number of wavelengths (i.e. number of illumination sources) that would need to be illuminated, as well as to determine the range of wavelengths from which the illumination sources may be chosen, so as to perform spectral analysis. The determined wavelengths and number of wavelengths are for illumination sources that may be implemented in an in-vivo device, such as device 100. After or during passage of an in-vivo device, e.g. device 100, through the lumen, the following calculations may be used in order to analyze the absorption of the chosen wavelengths by the tissue vs. absorption of the chosen wavelengths by the medium that is present between the in-vivo device and the tissue. Comparison between the absorption of the tissue vs. absorption of the medium may provide a more accurate estimate as to whether an illuminated lesion in the tissue is cancerous or benign.

Reference is now made to FIGS. 3A-3C, which illustrate, respectively, a schematic system for performing spectral analysis (3A), a schematic graph of medium absorption vs. wavelength (3B), and a schematic graph of tissue reflectance vs. wavelength (3C), as used in methods in accordance with an embodiment of the present invention. As can be seen from FIGS. 3B-3C, absorption coefficient of the medium and reflectance coefficient of the tissue depend on the illuminated wavelength $\lambda_i$, i.e. the medium absorption is denoted by $\alpha_{\lambda,i}$, and the tissue reflectance is denoted by $R_{\lambda,i}$. The following equation may be used in order to calculate the tissue reflectance $R_{\lambda,i}$ in various wavelengths, which may indicate the tissue spectral characteristics (e.g. whether an illuminated lesion is cancerous or benign):

$$I_{\lambda_i} = \frac{I_{0\lambda i} \cdot R_{\lambda_i} \cdot A}{D^2} \cdot e^{(-2D \cdot \alpha_{\lambda_i})} \quad \text{(vi)}$$

wherein:
$I_{0\lambda,i}$ is the illumination intensity of the illumination source, which may illuminate at wavelength $\lambda_i$;

$I_{\lambda,i}$ is the intensity of the light that is collected by the image sensor contained within the in-vivo device ($I_{\lambda,i}$ depends on the optical design, e.g. on f number, and on the imager design, e.g.

pixel size, in addition to depending on the illuminated wavelength. However, since the optical design and imager design are fixed and thereby unchanged for any illuminated wavelength, they may be neglected from the calculations);

D is the distance between the in-vivo device and the tissue (FIG. 3A);

$R_{\lambda,i}$ is the tissue reflectance, which depends on illuminated wavelength and tissue composition; and A is the Albedo coefficient, which stands for the tissue reflectance as dependant on the angle of incidence (A is substantially not dependent on wavelength).

In order to estimate the tissue reflectance in the blood absorption wavelength range, specific wavelengths, e.g. $\lambda 1$-$\lambda 4$, should be implemented into equation (iv), as such:

$$I_{\lambda_1} = \frac{I_{0\lambda i} \cdot R_{\lambda_1} \cdot A}{D^2} \cdot e^{(-2D \cdot \alpha_{\lambda_1})} \quad (1)$$

$$I_{\lambda_2} = \frac{I_{0\lambda i} \cdot R_{\lambda_2} \cdot A}{D^2} \cdot e^{(-2D \cdot \alpha_{\lambda_2})} \quad (2)$$

$$I_{\lambda_3} = \frac{I_{0\lambda i} \cdot R_{\lambda_3} \cdot A}{D^2} \cdot e^{(-2D \cdot \alpha_{\lambda_3})} \quad (3)$$

$$I_{\lambda_4} = \frac{I_{0\lambda i} \cdot R_{\lambda_4} \cdot A}{D^2} \cdot e^{(-2D \cdot \alpha_{\lambda_4})} \quad (4)$$

Equation (3) and (4) may be divided and manipulated in order to reach equation (6):

$$\ln\left(\frac{I_{\lambda_3}}{I_{\lambda_4}}\right) = -2D(\alpha_{\lambda 4} - \alpha_{\lambda_3}) \quad (6)$$

FIG. 3A illustrates the distance D between the in-vivo device and the tissue. The tissue may have different reflectance for different wavelengths. When distance D is known by, for example, grayness level (as described above), and $I_{\lambda,i}$ may be known from the collected image level per any wavelength, then the difference ($\alpha_{\lambda,4}$-$\alpha_{\lambda,3}$) may be extracted. The difference between the absorption coefficient of the medium at wavelength $\lambda_4$ and the absorption coefficient of the medium at wavelength $\lambda_3$ may represent a slope of one of the curves illustrated in FIG. 3B. As shown in FIGS. 3B-3C, the medium absorbs light at wavelengths $\lambda_4$ and $\lambda_3$ (FIG. 3B), while the tissue, having high reflectance, thus absorbs substantially no light at these wavelengths, as can be observed by the curve between $\lambda_4$ and $\lambda_3$, which is elevated and constant (FIG. 3C).

FIG. 3B illustrates the absorption coefficient of the medium vs. wavelength for different medium concentrations. As illustrated in FIG. 3B, the higher the medium concentration, the more light it absorbs. The absorption coefficient of the medium is a function of both the illuminated wavelength and the medium's concentration. In some embodiments, the medium may be bile, thus the dependency of its absorption coefficient on the illuminated wavelengths and on different concentrations may be known, thereby producing FIG. 3B. In other embodiments, other mediums may be present in-vivo, and their absorption coefficient dependency on the illuminated wavelength may be studied in order to produce graphs similar to the ones illustrated in FIG. 3B. When comparing the difference ($\alpha_{\lambda,4}$-$\alpha_{\lambda,3}$) to the corresponding slope of one of the curves in FIG. 3B, the concentration of the medium (e.g. bile) may be found, thus the absorption coefficient per wavelength may be extracted from the corresponding curve. Once the absorption coefficient per wavelength is known, the tissue reflectance ($R_{\lambda,i}$) and Albedo (A) may be extracted by using any two equations selected from equations (1) to (4).

In some embodiments, the distance D between the in-vivo device and the tissue may not be known or may not be calculated by methods such as grayness level, thus other calculation should be done in order to extract tissue reflectance per wavelength ($R_{\lambda,i}$). Calculations with an additional wavelength, e.g. $\lambda_5$, are needed:

$$I_{\lambda_5} = \frac{I_{0\lambda i} \cdot R_{\lambda_5} \cdot A}{D^2} \cdot e^{(-2D \cdot \alpha_{\lambda_5})} \quad (5)$$

In some embodiments, similarly to $\lambda_3$ and $\lambda_4$, $\lambda_5$ is also chosen as a wavelength at which the medium absorbs light, while the tissue substantially absorbs no light.

Equations (5) and (4) are then manipulated in order to achieve an equation similar to that of equation (6):

$$\ln\left(\frac{I_{\lambda_4}}{I_{\lambda_5}}\right) = -2D(\alpha_{\lambda 5} - \alpha_{\lambda_4}) \quad (7)$$

Since D is unknown, equation (6) is divided by equation (7) in order to reduce the dependency of the equations on D:

$$\frac{\ln\left(\frac{I_{\lambda_3}}{I_{\lambda_4}}\right)}{\ln\left(\frac{I_{\lambda_4}}{I_{\lambda_5}}\right)} = \frac{(\alpha_{\lambda_4} - \alpha_{\lambda_3})}{(\alpha_{\lambda_5} - \alpha_{\lambda_4})} \quad (8)$$

Equation (8) may provide a ratio at different wavelengths between slopes of any of the curves in FIG. 3B. The concentration of the medium corresponding to the slopes' ratio may be inferred from the curves' shapes, thus the absorption coefficient per wavelength may be extracted from the concentration graph. Once the absorption coefficient per wavelength is known, distance D may be found from either of equations (6) and (7). The tissue reflectance $(R_{\lambda,i})$ and Albedo (A) may be extracted by using any two equations selected from equations (1) to (5).

According to other embodiments, the tissue reflectance $(R_{\lambda,i})$ may be calculated by, for example, dividing equation (2) by equation (1), thus reducing the dependency on A, and remaining with the ratio of $R_{\lambda,2}/R_{\lambda,1}$. This ratio may be compared with known graphs of tissue reflectance, e.g. blood reflectance vs. wavelength, for different concentrations of blood. Such a graph of tissue reflectance vs. wavelength is illustrated in FIG. 3C. Since the ratio $R_{\lambda,2}/R_{\lambda,1}$ can only correspond to one of these curves, i.e. to one blood concentration, the concentration of blood that corresponds to the ratio of tissue/blood reflectance may be determined, and thus the tissue/blood reflectance per $\lambda_2$ and per $\lambda_1$ may be determined.

Therefore, in order to perform spectral analysis with an in-vivo device, e.g. device 100, in embodiments where distance D (between the in-vivo device and the tissue, FIG. 3A) is known or may be calculated, the in-vivo device is required to illuminate with at least two illumination sources having a central wavelength at which the medium absorbs light, while the tissue substantially absorbs no light (e.g. $\lambda_3$ and $\lambda_4$). In addition, the device is required to illuminate with at least two illumination sources having a central wavelength at which both the medium and the tissue absorbs the light (e.g. $\lambda_1$ and $\lambda_2$). Whereas, in embodiments where D is unknown, the device is required to illuminate in at least one additional central wavelength at which the medium absorbs light, while the tissue substantially absorbs no light (e.g. $\lambda_5$).

Figure 4:
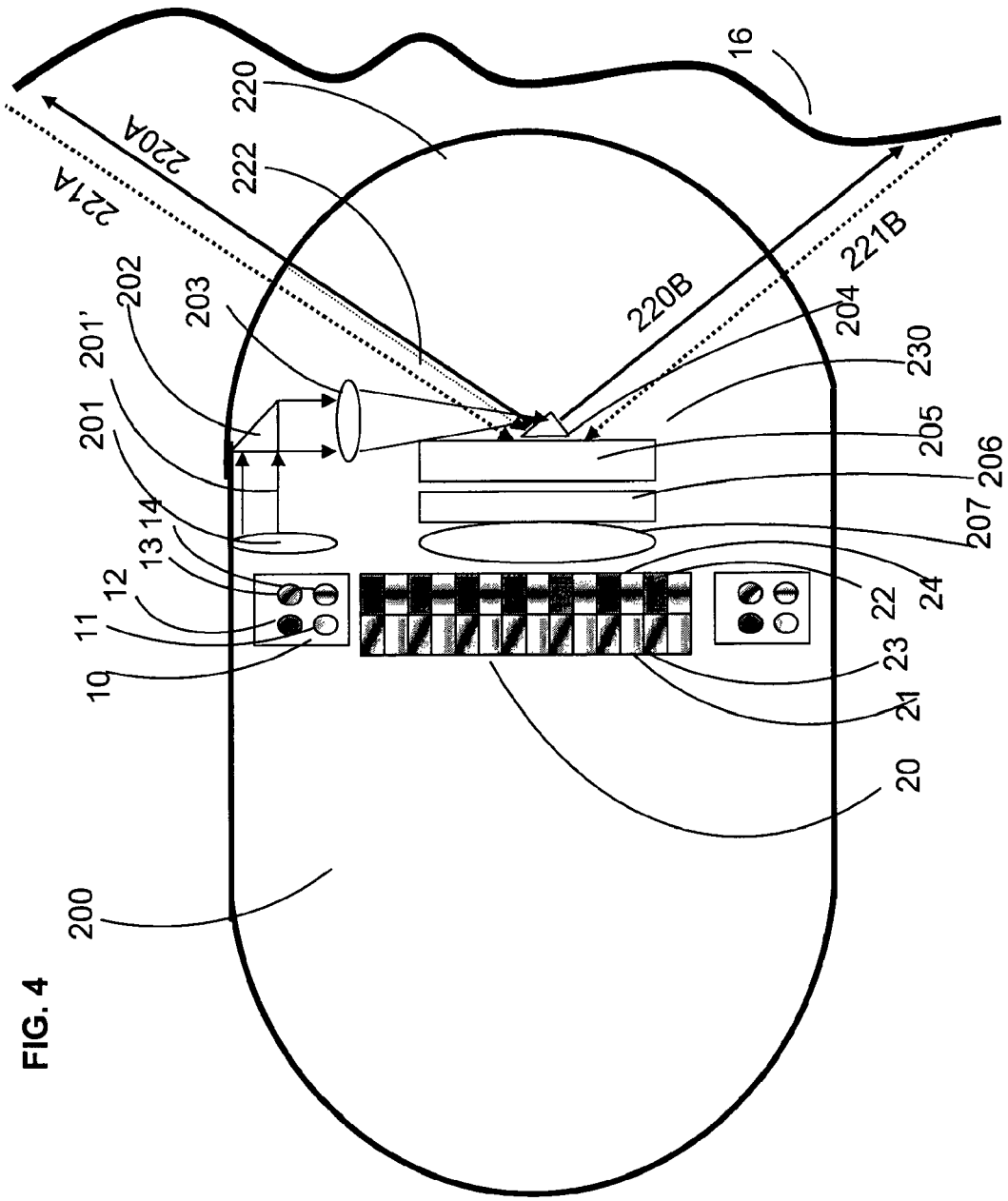
FIG. 4 illustrates a schematic lengthwise sectional view of an in-vivo imaging device in accordance with a third embodiment of the present invention.

Reference is now made to FIG. 4, which illustrates a schematic lengthwise sectional view of an in-vivo imaging device 200 in accordance with a third embodiment of the present invention. The in-vivo device 200 according to FIG. 4 is similar to device 100 (FIG. 1) in that they both have the ability to determine concentration of blood in tissue 16. Methods of calculating blood concentration as described above with regards to device 100 may be used with regards to device 200 as well. However, device 200 has the additional advantage of acquiring elastic scattering light data and may thus provide information on the sizes of nuclei and their arrangement within the tissue 16, which may teach on the stage of progression of pathology, i.e. on pathology severity.

According to some embodiments, device 200 may comprise light-guiding means for directing light from illumination unit 10 so that the light is directed substantially from a point positioned on the optical axis of device 200 proximal to lens 205 and between it and window 220, towards tissue 16. According to one embodiment this may be achieved by using an arrangement comprising collimating lens 201, folding mirror 202 and condensing lens 203, which may guide light from illumination unit 10 onto cone mirror 204. In some embodiments, collimating lens 201 may be positioned between illumination unit 10 and window 220. Collimating lens 201 may cause light emitted from illumination unit 10 to emerge in a parallel beam 201'. The parallel beam of light 201' may then reach a folding mirror 202, which may shift the direction of the beam in substantially 90 degrees, thus redirecting the light towards condensing lens 203, which may condense the light beam and may direct it towards a mirror 204 having a conical shape, hereinafter a cone mirror. In some embodiments, cone mirror 204 may comprise either a flat or a curved surface.

When a window through which light is transmitted has the shape of a sphere, or at least a part of the window is spherically shaped, the sensing of stray light, e.g. inner light reflection, may be avoided by locating the illumination source at the center of curvature of the sphere or spherically shaped area, or by causing light to be projected from the center of the sphere, as may be done with the cone mirror 204 disposed at the center of the sphere. Thus, all light reflections are reflected back towards the center of the sphere only (or towards the cone mirror alone), and not towards other components within the sphere. For example, any of the lenses of optical system 230 (e.g. lenses 205, 206 and 207), which are located within the concave side of spherical window 220, may not be exposed to the reflecting light, e.g. light beam 222, thus image blurring is avoided. Therefore, device 200 may have a spherical shape, or may at least comprise a spherical window, which at least illumination unit 10, optical system 230 and image sensor 20 may be located within its concave side. In some embodiments, since cone mirror 204 is located at the center of the spherical housing of device 200, or at the center of the spherical optical window 220 of device 200, any light reflections may be reflected back onto the cone mirror 204, thus avoiding any image blurring. Therefore, in some embodiments, cone mirror 204 is located on the optical axis of system 230, at the center of spherical window 220, and imager 20 may collect light reflected from the tissue, and not collect light reflected from within the sphere.

Cone mirror 204 may cause illumination projected onto it from illumination unit 10, to reach tissue 16 at an angle similar to the angle of the field of view (FOV) of imager 20, e.g. the field of illumination (FOI) is substantially overlapping that of the FOV. This may ensure that illumination reflected and/or scattered from tissue 16 is substantially entirely viewed by imager 20. In order to collect as much as possible of the scattered light (which may provide indications of pathology characteristics, e.g. sizes and arrangement of nuclei within the tissue), scattered light should be collected at an angle substantially the same as the angle of illumination. According to FIG. 4, the field of illumination (FOI) is substantially overlapping that of the field of view (FOV), illumination angle and light acquisition angle being substantially the same.

For example, light projected onto cone mirror 204 may be then projected onto tissue 16 at any angle between light beam 220A and light beam 220B. According to some embodiments, the two beams 220A and 220B define the FOI. Light may then be reflected and scattered from tissue 16, at any angle between scattered light beam 221A and scattered light beam 221B. According to some embodiments, the two scattered light beams 221A and 221B define the FOV. As illustrated in FIG. 4, the FOI is substantially overlapping that of the FOV, thus the portion of collected scattered light is at maximum.

In some embodiments, illumination unit 10 may comprise a plurality of illumination sources, e.g. illumination sources 11, 12, 13, and 14 as described above (FIG. 1). Other combinations of light sources may be used.

In some embodiments, scattered light (e.g. scattered light beams 221A and 221B) may pass through an optical system that may focus the scattered light onto an imager 20. Such an optical system may comprise a plurality of lenses, e.g. lenses 205, 206, and 207. Other optical elements for focusing the scattered light onto imager 20 may be used.

Diseases in the gastrointestinal tract are often expressed in the epithelium layer (100-200 µm deep), which is the layer closest to the tissue surface. Light reflected and scattered from the epithelium layer is polarized, whereas light reflected from inner layers is not. Thus, in order to differentiate between light that is reflected from the epithelium layer and light reflected from inner layers, a polarizer may be used. In some embodiments, optical element 206 may comprise a polarizer. When optical element 206 comprises a polarizer, illumination unit 10 may also comprise a polarizer aligned with its polarization direction in the direction of polarization of the received polarized light at element 206. The polarizer for polarizing the light emitted from illumination unit 10 may be located either between collimating lens 201 and folding mirror 202, or between folding mirror 202 and condensing lens 203. A polarizer may be included in device 200, in order to collect light reflected and scattered from the tissue layer closest to the tissue surface, alone.

In some embodiments, image sensor 20 may comprise standard RGB filters (e.g. Bayer filter arrangement), and illumination sources 11, 12, 13, and 14 may illuminate in an alternating mode. Another illuminating and light collecting scheme may be used, similar to the one illustrated in FIG. 2. In some embodiments, the different illuminating periods may be substantially the same. In other embodiments, different illuminating time periods may be used.

In other embodiments, imager 20 may comprise a few filters that correspond to the illumination sources' wavelengths. Such filters may be narrow band filters, interference filters or diffractive optical element (DOE) filters. As described above (FIG. 1), imager 20 may comprise filters 21, 22, 23, and 24, where a range of wavelengths passing through each correspond to the wavelength of the light of illumination sources 11, 12, 13, and 14, respectively. In some embodiments, since imager 20 comprises filters dedicated to allow passage of light at a range of wavelengths, which correspond to the wavelengths at which light is illuminated, there is no need for illuminating in an alternating mode, but rather all illumination sources may illuminate at once. A color image may be created from the light collection done by imager 20, and thus presence and severity of polyps may be inferred, as well as their in-vivo location along the lumen.

Figure 5:
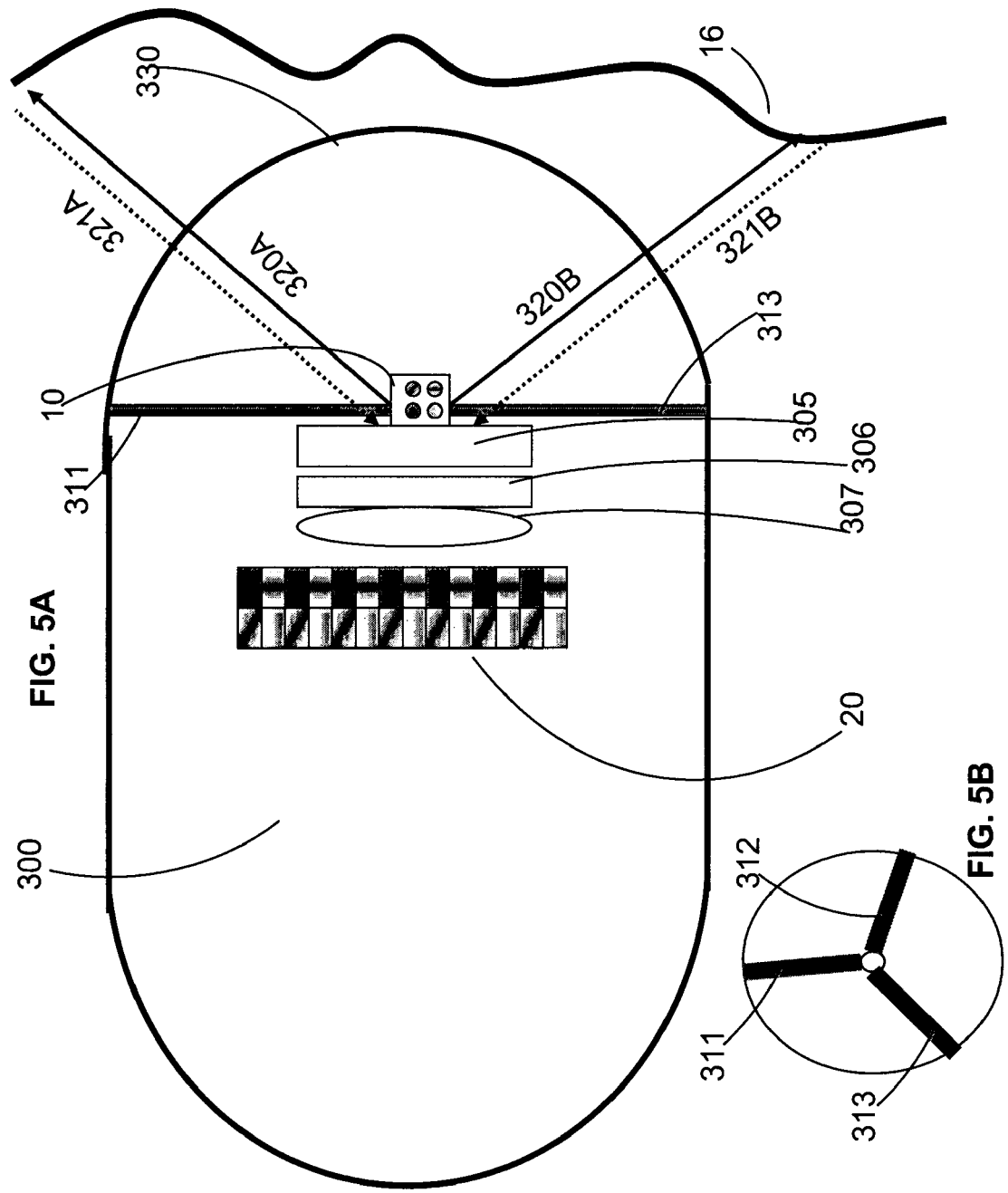
FIGS. 5A-5B illustrate a schematic lengthwise sectional view, and a respective cross-sectional front view of an in-vivo imaging device, in accordance with a fourth embodiment of the present invention.
Figure 6:
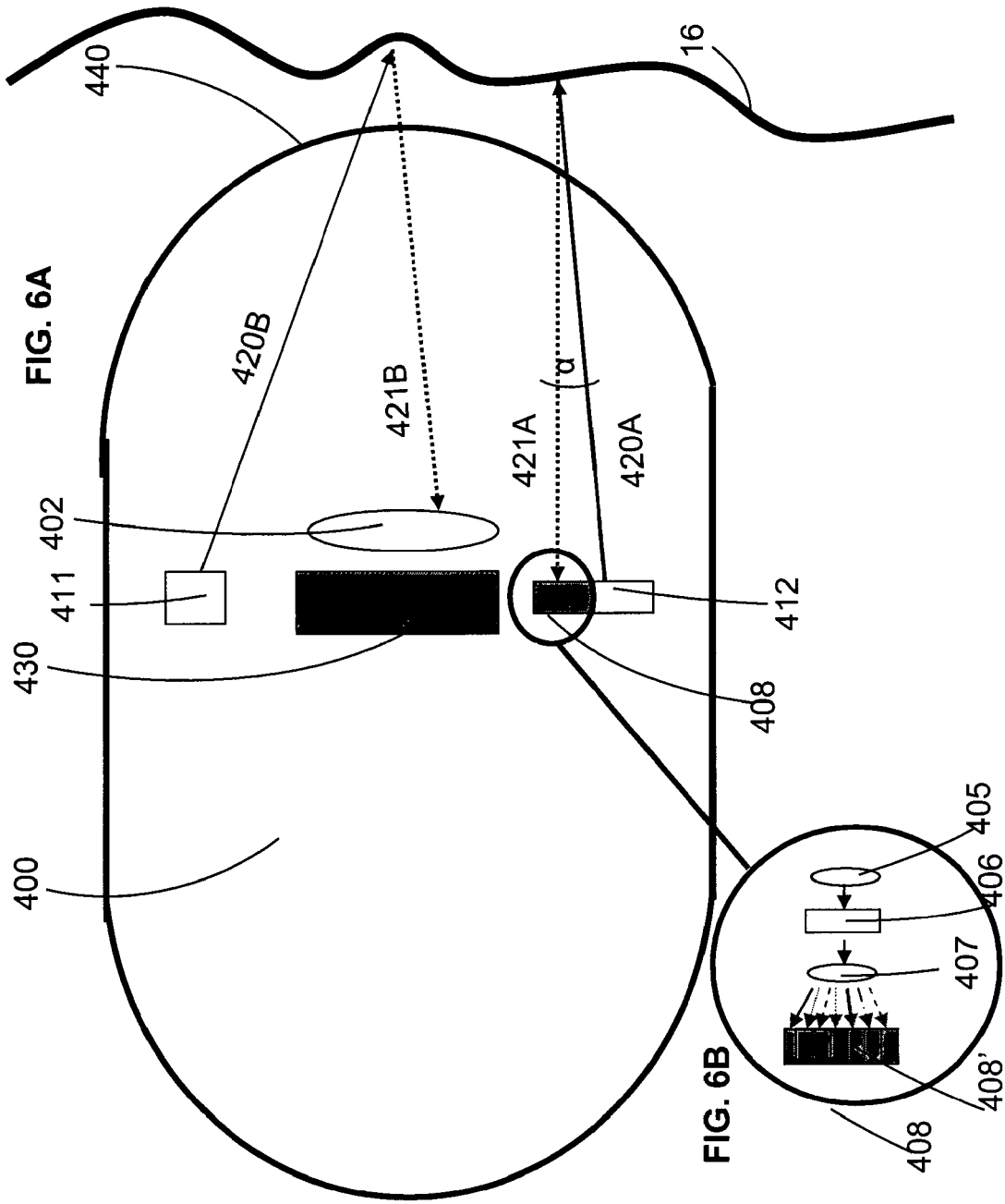
FIGS. 6A-6B illustrate a schematic lengthwise sectional view of an in-vivo imaging device, and a respective partial exploded view of one of the device's components, in accordance with a fifth embodiment of the present invention.

Reference is now made to FIGS. 5A-5B, which illustrate a schematic lengthwise sectional view, and a respective cross-sectional front view of an in-vivo imaging device, respectively, in accordance with a fourth embodiment of the present invention. According to some embodiments, device 300 may comprise a spherical window 330 behind which are positioned an illumination unit 10, an optical system (which may comprise several lenses, e.g. lenses 305, 306, and 307), and image sensor 20.

Diseases in the gastrointestinal tract are often expressed in the epithelium layer (100-200 µm deep), which is the layer closest to the tissue surface. Light reflected and scattered from the epithelium layer is polarized, whereas light reflected from inner layers is not. Thus, in order to differentiate between light that is reflected from the epithelium layer and light reflected from inner layers, a polarizer may be used. In some embodiments, lens 306 may comprise a polarizer. When lens 306 comprises a polarizer, illumination unit 10 may also comprise a polarizer aligned with its polarization direction in the direction of polarization of the received polarized light at lens 306. The polarizer for polarizing the light emitted from illumination unit 10 may be located between illumination unit 10 and window 330. A polarizer may be included in device 300, in order to collect light reflected and scattered from the tissue layer closest to the tissue surface, alone.

As described above (FIG. 4), in order to avoid stray light within a device, the device should either have a spherical shape, or should have a spherically shaped section behind which the illumination source is positioned. Furthermore, light from the illumination source should be projected onto the tissue from the center of the sphere. As can be seen in FIG. 5A, device 300 may comprise an illumination unit 10 that may be located at the center of the spherical window 330. Since illumination unit 10 is located at the center of the spherical window 330, the detection of stray light, i.e. inner reflections off the concave side of the window 330, may be avoided. Inner reflections may be reflected back onto the center of the sphere, where illumination unit 10 is located, and not reflected back onto other components that are located within the concave side of spherical window 330, thus image blurring may be avoided.

In addition to avoiding stray light, the location of illumination unit 10 is also beneficial in collecting substantially all of the light that is scattered in response to the light illuminated by illumination unit 10. As described before (FIG. 4), when the FOI is substantially overlapping that of the FOV, almost all of the scattered light may be collected by image sensor 20. The FOI is defined by the angle between light beams 320A and 320B, while the FOV is defined by the angle between scattered light beams 321A and 321B. As may be seen from FIG. 5A, the FOI is substantially overlapping that of the FOV, thus substantially all scattered light may be collected by imager 20.

According to some embodiments, device 300, like device 200, may provide information on both reflected and scattered light. Thus, device 300 may provide information on sizes and arrangement of nuclei in the imaged tissue, in addition to blood concentration (done by methods described in FIG. 1), both of which may indicate on severity of pathology as well as its stage of progression.

According to some embodiments, as illustrated in FIG. 5B, illumination unit 10, which is located at the center of spherical window 330, may be held in place by several arms, e.g. arms 311, 312, 313). Other numbers of arms may be used. According to some embodiments, the arms holding illumination unit 10 in the center of the spherical window 330 may obstruct some of the FOV, but the width of the arms may be chosen as such to obstruct as minimum image area as possible. In some embodiments, in order to obstruct less of the image area, there may be only two arms instead of three. The arms 311, 312, and 313 may connect between the illumination unit 10 and the spherical window 330 so as to fixate the location of the illumination unit 10 with respect to the spherical window 330, such that it is located at the center of the spherical window 330. In some embodiments, electrical wires for transferring power to the illumination unit 10 from internal power source (not shown) of device 200 may be passed through the holding arms (311, 312 and/or 313).

According to some embodiments, device 300 may comprise an illumination unit 10 which may comprise a matrix of light sources, e.g. light sources 11, 12, 13, and 14, as described in FIG. 1. Other numbers of illumination sources and other illumination sources' wavelengths than the ones described above may be used. The size of illumination unit 10 may be as small as 0.7 mm length over 0.7 mm width, thus minimizing the image obstruction caused by illumination unit 10.

According to some embodiments, device 300 may comprise imager 20. In some embodiments, imager 20 may comprise standard RGB filters (e.g. Bayer filter arrangement), and illumination sources 11, 12, 13, and 14, which illumination unit 10 may be comprised of, may illuminate in an alternating mode. In other embodiments, imager 20 may comprise filters (long pass, short pass, wide band pass filters, or a combination thereof) and the illumination sources may illuminate in groups of three illumination sources illuminating simultaneously with one another (FIG. 2). In some embodiments, the different illuminating groups may illuminate for substantially the same time period. In other embodiments, different illuminating time periods may be used for each of the groups.

In other embodiments, imager 20 may comprise a few filters, where a range of wavelengths passing through each filter correspond to the wavelength of the light of each illumination sources. Such filters may be narrow band filters, interference filters or diffractive optical element (DOE) filters. As described above (FIG. 1), imager 20 may comprise filters 21, 22, 23, and 24, where a range of wavelengths passing through each of the filters correspond to the wavelength of the light of illumination sources 11, 12, 13, and 14, respectively. In some embodiments, since imager 20 comprises filters dedicated to allow passage of light at a range of wavelengths, which correspond to the wavelengths at which light is illuminated, there is no need for illuminating in an alternating mode, but rather all illumination sources may illuminate at once. A color image may be created from the light collection done by imager 20, and thus presence and severity of polyps may be inferred.

Reference is now made to FIGS. 6A-6B, which illustrate respectively a schematic lengthwise sectional view of an in-vivo imaging device, and an exploded view of one of the device's components, in accordance with a fifth embodiment of the present invention. According to some embodiments, device 400 may comprise an image sensor 430, an optical system 402, and at least two illumination sources 411, and 412, which may be positioned within the concave side of window 440. According to other embodiments device 400 may comprise other numbers of illumination sources, e.g. device 400 may comprise four illumination sources located symmetrically around imager 430, e.g. each illumination source is located at the same distance from imager 430.

Diseases in the gastrointestinal tract are typically expressed in the epithelium layer (100-200 μm deep), which is the closest to the tissue surface. Light reflected and scattered from the epithelium layer is polarized, whereas light reflected from inner layers is not. Thus, in order to differentiate between light that is reflected from the epithelium layer and light reflected from inner layers, a polarizer may be used. In some embodiments, device 400 may comprise a polarizer (not shown), which may be positioned in front of imager 430, e.g. between optical system 402 and image sensor 430. When image sensor 430 has a polarizer located in front of it, illumination source 411 may also comprise a polarizer aligned with its polarization direction in the direction of polarization of the received polarized light at the polarizer located in front of imager 430. The polarizer for polarizing the light emitted from illumination source 411 may be located between illumination source 411 and window 440. A polarizer may be included in device 400, in any location where it can collect light only reflected and scattered from the tissue layer closest to the tissue surface.

In some embodiments, illumination sources 411 and 412 (and/or others) may be white light LEDs. Illumination source 411 may illuminate tissue 16. The reflected light may be collected by optical system 402, which may comprise of a focusing lens, onto image sensor 430 in order to create a white light image of the illuminated area of tissue 16. For example, light beam 420B may be illuminated onto tissue 16 by illumination source 411, and the reflected light beam 421B may be collected by optical system 402 and projected onto imager 430 to create an image of that illuminated area of tissue 16.

In some embodiments, device 400 may further comprise a mini-spectrometer 408, which may collect scattered light off tissue 16. Mini-spectrometer 408 may be located in close proximity to illumination source 412. Illumination sources 411 and 412 may operate in alternating mode, such that when illumination source 411 illuminates tissue 16, illumination source 412 does not operate, and an image is acquired by imager 430. Whereas, when illumination unit 412 illuminates tissue 16, illumination source 411 does not operate, and thus spectral information may be collected by mini-spectrometer 408. For example, illumination source 412 may illuminate an area of tissue 16 with light beam 420A. Scattered light 421A from substantially that same illuminated area of tissue 16 may then be collected by mini-spectrometer 408, which may analyze the scattered light and may thus provide information on pathology characteristics. In order to ensure that substantially all of the light emitted by illumination source 412 is collected by mini-spectrometer 408, i.e. that the area being analyzed by the mini-spectrometer 408 is substantially the same as the illuminated tissue area, angle α needs to be of a minimum size. In some embodiments, the angle α, which is defined between a light beam projected from illumination source 412 onto tissue 16 (e.g. beam 420A) and the light beam scattered from tissue 16 and collected by mini-spectrometer 408 (e.g. beam 421A) should be no larger than 10 degrees.

The presence of a pathology may be determined by observing the white light image created by imager 430, and then the scattered light, which that is collected by mini-spectrometer 408, may provide the additional details on pathology characteristics (e.g. polyp severity). According to some embodiments, mini-spectrometer 408 may comprise a plurality of pixels (e.g. 20 pixels) arranged as a line-detector or vector detector. Other mini-spectrometer arrangements may be used, for example, matrix type detectors.

In some embodiments, in order for the mini-spectrometer 408 to collect light that is already separated into various wavelengths, the scattered light needs to be separated by a few optical elements. As shown in FIG. 6B, mini-spectrometer 408 may comprise focusing lens 405, which may focus the scattered light (e.g. light beam 421A) onto a grating 406, which in practice separates the scattered light into the various wavelengths comprising it. In some embodiments, between the grating 406 and the detector 408' onto which the separated light is projected, there may be positioned an additional lens 407. Lens 407 may be a cylindrical focusing lens for focusing each separated light ray onto its corresponding position on the detector 408'. In some embodiments, cylindrical focusing lens 407 may receive the separated scattered light 421A after it was separated into specific wavelengths by the grating 406. The cylindrical focusing lens 407 may focus each of the separated specific wavelengths onto a different specific pixel, which is part of detector 408'.

According to the above description, scattered light (e.g. light ray 421A) may provide spectral information on one point in tissue 16. In order to acquire spectral information on an entire tissue line, which is part of tissue 16, the mini-spectrometer 408 may comprise a matrix type detector instead of only a vector-detector. That is, scattered light from a first point of a tissue line in tissue 16 may be separated into separate wavelengths (e.g. by grating 406). Each separated wavelength may be projected onto a corresponding pixel, when all of those pixels form the same first vector-detector. Scattered light from a second point of the same tissue line may also be separated into separate wavelengths (e.g. by grating 406). Each of the separated wavelengths of the second tissue point may be projected onto a different and corresponding pixel of the pixels that form a second vector-detector, and so on until the entire points of the same tissue line are analyzed. Thus, all scattered light beams from all the points that comprise the tissue line may be separated by, for example, using grating 406, and may be focused onto a plurality of vector-detectors, which constitute a matrix-detector.

In some embodiments, a lesion may be imaged by imager 430, while it may not be analyzed by mini-spectrometer 408, since light from illumination source 412 may not reach it (e.g. the lesion may be located opposite illumination source 411 and not opposite illumination source 412). However, although spectral information related to a lesion that is located outside the field of view of mini-spectrometer 408 may not be directly obtained, spectral information relating such a lesion may be obtained indirectly. An effect named "field effect", assumes that changes in blood concentration, for example, may begin at a location different than the exact location of the visible lesion. Assuming a lesion requires higher blood supply than normal tissue, new blood vessels must be created in order to transfer more blood to the area of the lesion. Such new blood vessels may pass through tissue areas located before and/or after the location of the visible lesion, along the same lumen. Thus, increase in blood concentration may be noted at tissue areas different than the lesion area, either before or after the lesion area, along the same lumen. Therefore, spectral characteristics of tissue that is located in proximity to a lesion may differ from spectral characteristics of normal tissue that is located at a farther distance from a lesion, and that may not be affected by changes in tissue occurring due to the lesion. In some embodiments, the distance between the visible lesion and the tissue location where spectral analysis is done, may be calculated based on grayness level obtained from the white light image. Tissue at different distances from a visible lesion may be estimated to have different spectral characteristics. Thus, spectral information obtained by mini-spectrometer 408 for tissue at one or more distances from an imaged lesion may be compared with a predetermined threshold in order to determine whether the lesion is cancerous or benign.

Figure 7:
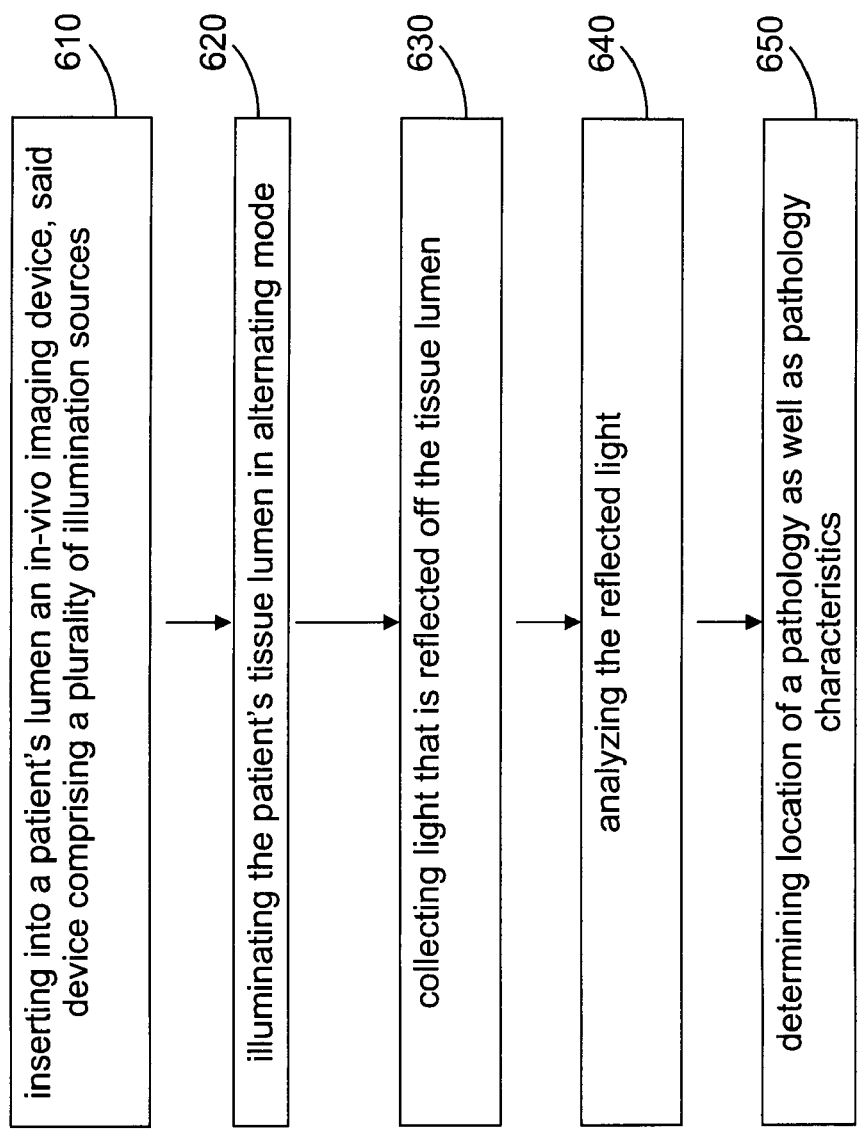
FIG. 7 illustrates a method for performing spectral analysis, in accordance with one embodiment of the present invention.

Reference is now made to FIG. 7, which illustrates a method for performing spectral analysis, in accordance with one embodiment of the present invention. According to some embodiments, a method for performing spectral analysis may comprise inserting into a patient's lumen an in-vivo imaging device that may comprise a plurality of illumination sources, where each illumination source may illuminate at a different wavelength (610). Such an in-vivo imaging device may be similar to device 100 (FIG. 1). In some embodiments, the method may comprise illuminating the patient's tissue in an alternating mode (620). In some embodiments, the in-vivo device may comprise an imager, which may comprise standard RGB filters, such that illuminating in an alternating mode is done by operating each of the plurality of illumination sources during a different time period. In other embodiments, the imager may comprise Color Enhancement filter types or Color Separation filter types disposed thereon. The color filters may be adapted to prevent overlap between illumination in the blue, green and red spectral regions collected by the imager. In such embodiments, the plurality of illumination sources may illuminate as groups of illumination sources. Each group may consist of one illumination source that illuminates in a wavelength corresponding to the blue region of the spectrum, one illumination source that illuminates in a wavelength corresponding to the green region of the spectrum, and one illumination source that illuminates in a wavelength corresponding to the red region of the spectrum. Every group of three different illumination sources as such, may illuminate simultaneously, thus shortening the illumination period as well as the light collection period.

In some embodiments, the method may further comprise collecting light that is reflected off the tissue lumen (630). This may be done by an imager contained within the device. In some embodiments, the method may comprise analyzing the reflected light (640) and determining location of a pathology as well as determining characteristics of the pathology (650). In some embodiments, the step of analyzing the reflected light may comprise creating a color image. From the color image, the presence of a pathology may be determined, together with its location along the lumen. Furthermore, characteristics of the pathology, e.g. its blood concentration, may also be inferred from the color image, for example, by examining its grayness levels at the different imaged areas, the imaged lesion area and its imaged surroundings (as described above with regards to FIG. 1).

In some embodiments, the step of analyzing the scattered and reflected light may be performed by either an analyzing unit or by an operator of the in-vivo device. An analyzing unit may be part of the in-vivo device, or may be located externally to it.

Figure 8:
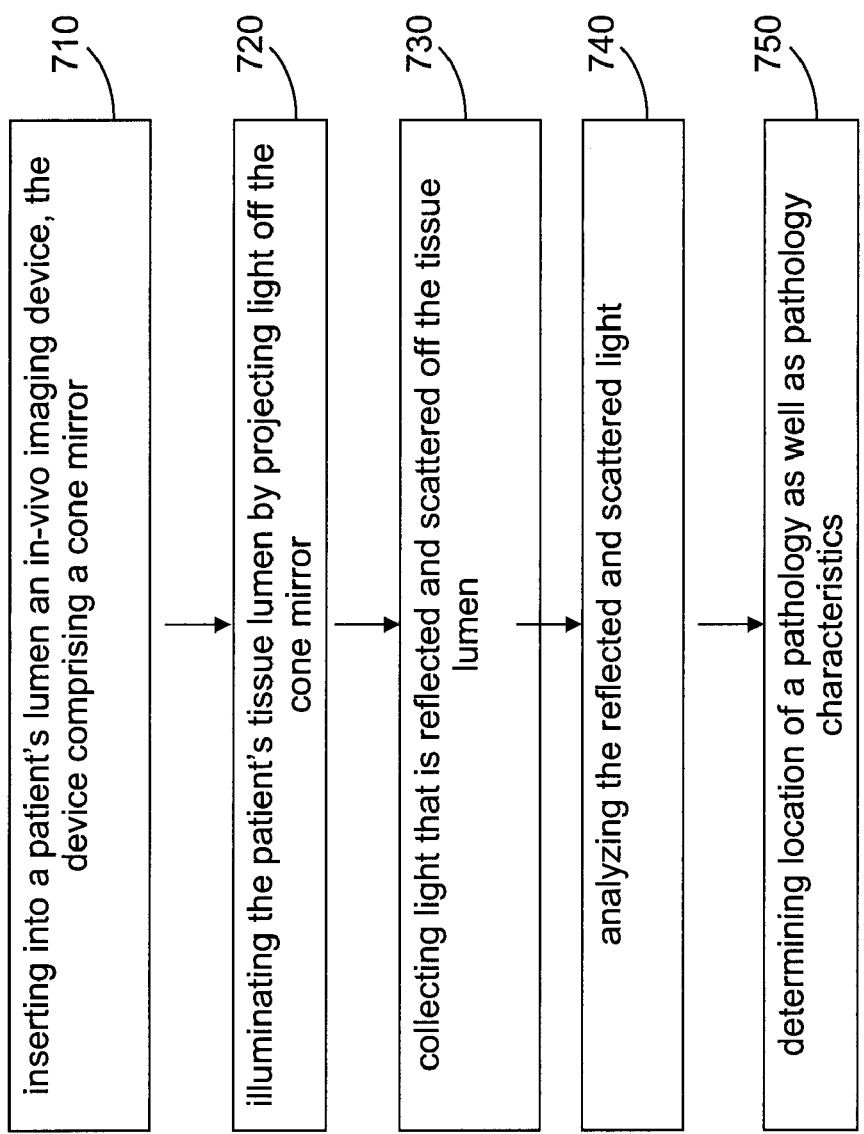
FIG. 8 illustrates a method for performing spectral analysis, in accordance with another embodiment of the present invention.

Reference is now made to FIG. 8, which illustrates a method for performing spectral analysis, in accordance with another embodiment of the present invention. According to some embodiments, a method for performing spectral analysis may comprise inserting into a patient's lumen an in-vivo imaging device that may comprise a cone mirror (710). Such an in-vivo device may be similar to device 200 (FIG. 4). In some embodiments, the method may comprise illuminating the patient's tissue lumen by projecting light off the cone mirror (720). As described above regarding FIG. 4, light from the at least four illumination sources 11, 12, 13, and 14, may be directed onto the cone mirror, which may then project the light towards the tissue.

According to some embodiments, the method may comprise collecting light that is reflected and scattered off the tissue lumen (730), as well as the step of analyzing the reflected and scattered light (740). In some embodiments, the method may comprise the step of determining the location of a pathology as well as pathology characteristics (750). In some embodiments, the step of analyzing the scattered and reflected light may be performed by either an analyzing unit or by an operator of the in-vivo device. An analyzing unit may be part of the in-vivo device, or may be located externally to it.

In some embodiments, the analyzing step may comprise acquiring a color image that may be acquired by the reflected and scattered light. In some embodiments, determining the location of the pathology along the lumen may be performed by observing the color image. In some embodiments, determining the pathology characteristics may be done by analyzing the scattered light's wavelengths from which the color is made of. Since different materials inside the body may have a spectral signature that might change due to presence of pathology, and since changes in such materials' arrangement inside the body may occur due to the presence of a pathology, the specific wavelengths may indicate the presence of a pathology, or even the pathology characteristics.

Figure 9:
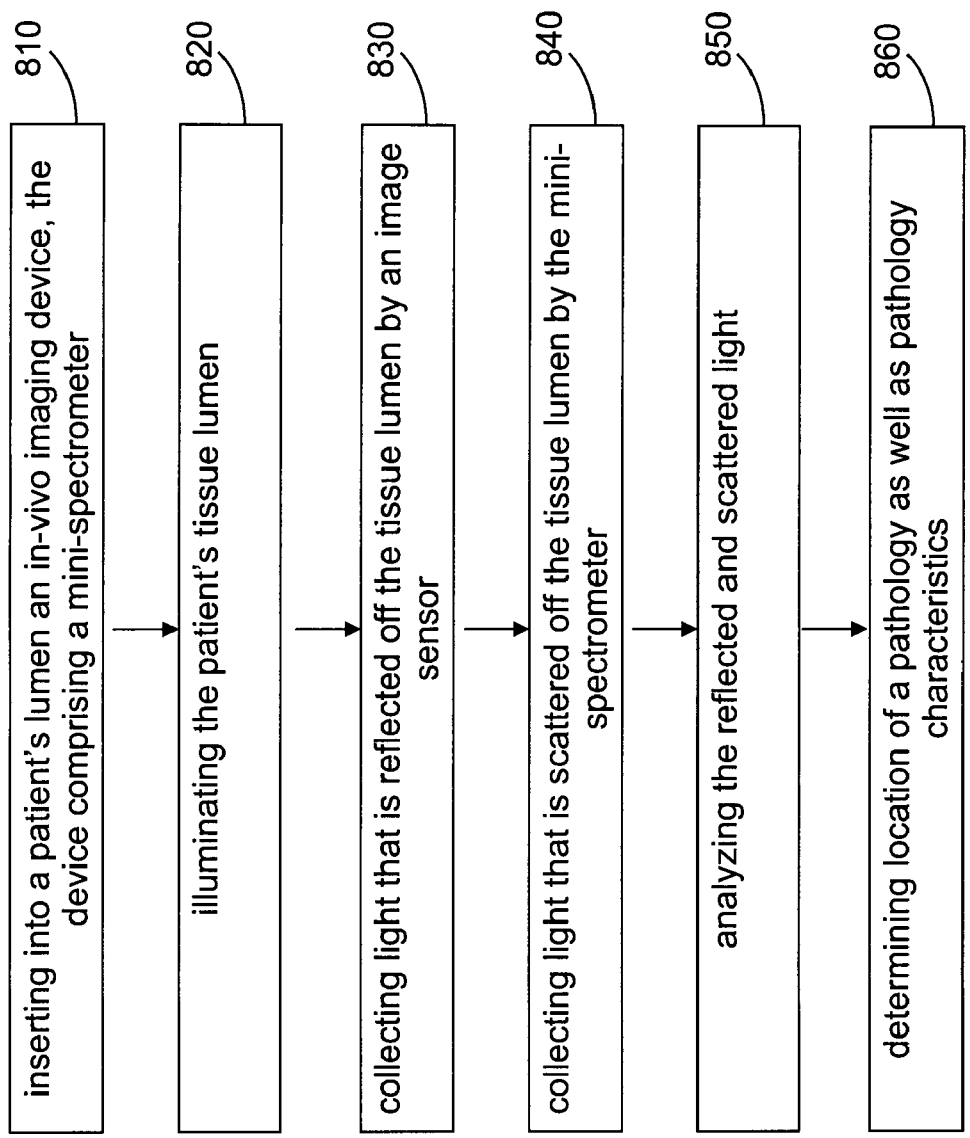
FIG. 9 illustrates a method for performing spectral analysis, in accordance with yet another embodiment of the present invention.

Reference is now made to FIG. 9, which illustrates a method for performing spectral analysis, in accordance with yet another embodiment of the present invention. In some embodiments, inserting into a patient's lumen an in-vivo imaging device that comprises a mini-spectrometer (810). Such an in-vivo device may be similar to device 400 (FIG. 6A). In some embodiments, the method may comprise illuminating the patient's tissue lumen (820). The illumination sources used may be illuminating in white light.

In some embodiments, the method may comprise collecting light that is reflected off the tissue lumen by the image sensor within the device (830). A white light image may be acquired by the image sensor. The method may further comprise the step of collecting light that is scattered off the tissue lumen by the mini-spectrometer (840). In some embodiments, there may be at least one illumination source for illuminating the tissue, and the reflected light may be acquired by an image sensor for obtaining a white light image, whereas, when that at least one illumination source does not operate, another illumination source, which may be located in close proximity to the mini-spectrometer, may illuminate the tissue and scattered light may be collected by the mini-spectrometer. These at least two illumination sources may illuminate in an alternating mode instead of simultaneously (as described above in FIG. 6A). In some embodiments, the method may comprise analyzing the reflected and scattered light (850). In some embodiments, the method may further comprise the step of determining location of a pathology as well as determining the pathology characteristics (860). In some embodiments, determining the location of the pathology may be performed by observing the white light image, which may be acquired by the image sensor. In some embodiments, determining the pathology characteristics may be done by analyzing the scattered light's wavelengths collected by the mini-spectrometer. As described with regards to FIGS. 6A-6B, the mini-spectrometer may either comprise a vector-detector, which may collect scattered light from a point in the tissue, or a matrix detector, which may collect scattered light from a tissue line.

While the present invention has been described with reference to one or more specific embodiments, the description is intended to be illustrative as a whole and is not to be construed as limiting the invention to the embodiments shown. It is appreciated that various modifications may occur to those skilled in the art that, while not specifically shown herein, are nevertheless within the scope of the invention.

What is claimed is:

1. A method for performing spectral analysis of a lumen tissue to determine blood concentration using an in-vivo imaging device, said method comprising:
collecting a plurality of wavelengths of light that are reflected off the lumen tissue by an image sensor, thereby generating spectral information of the lumen tissue, wherein at least two wavelengths $\lambda_1$ and $\lambda_2$ are wavelengths having a high level of absorbance in hemoglobin, and at least two wavelengths $\lambda 3$ and $\lambda 4$ A are selected from a range of wavelengths having a low level of absorbance in hemoglobin;

calculating, by a processor, a difference between the absorption coefficient of the medium surrounding the tissue at wavelength $\lambda 4$ and the absorption coefficient of the medium at wavelength $\lambda 3$;

calculating, by the processor, the absorption coefficient per wavelength by comparing the difference between absorption coefficient per wavelength $\lambda 4$ and absorption coefficient per wavelength $\lambda 3$ to a graph illustrating absorption coefficient of said medium vs. wavelength;

calculating, by the processor, light reflections for wavelengths $\lambda_1$ and $\lambda_2$ representing grayness level, using absorption coefficient of the medium per wavelengths $\lambda_1$ and $\lambda_2$;

calculating, by the processor, a ratio between the light reflections from the tissue for wavelengths $\lambda_1$ and $\lambda_2$; and determining, by the processor, blood concentration in the tissue from said ratio between light reflections.

2. The method according to claim 1, wherein the step of calculating a difference between the absorption coefficient of the medium surrounding the tissue at wavelength $\lambda_4$ and the absorption coefficient of the medium at wavelength $\lambda_3$ is done by applying the following equation per each wavelength $\lambda_3$ and $\lambda_4$:

$$I_{\lambda_i} = \frac{I_{0\lambda_i} \cdot R_{\lambda_i} \cdot A}{D^2} \cdot e^{(-2D \cdot \alpha_{\lambda_i})} \quad \text{(vi)}$$

wherein:
$I_{0\lambda_i}$ is the illumination intensity of the illumination source, which illuminates at wavelength $\lambda_i$;
$I_{\lambda,i}$ is the intensity of the light that is collected by the image sensor;
D is the distance between the tissue and the device for collecting the light reflections;
$R_{\lambda,i}$ is the reflection from the tissue at wavelength $\lambda_i$;
$\alpha_{\lambda,i}$ is the absorption coefficient of the medium, which depends on the illuminated wavelength $\lambda i$; and
A is the Albedo coefficient, which stands for the tissue reflectance as dependent on the angle of incidence;
and dividing the equations thus reaching equation (6):

$$\ln\left(\frac{I_{\lambda_3}}{I_{\lambda_4}}\right) = -2D(\alpha_{\lambda 4} - \alpha_{\lambda_3}). \quad \text{(6)}$$

3. The method according to claim 2, wherein the step of calculating light reflections for wavelengths $\lambda_1$ and $\lambda_2$ is done by applying equation (vi) per each wavelength $\lambda_1$ and $\lambda_2$.

4. The method according to claim 2, wherein distance D is calculated by applying equation (vi) per an additional wavelength $\lambda_5$, which is selected from a range of wavelengths that their absorbance in hemoglobin is of a low level, and which is different from $\lambda_3$ and $\lambda_4$, and by further manipulating equation (vi) per wavelengths $\lambda_3$, $\lambda_4$, and $\lambda_5$ to calculate the absorption coefficient of the medium per wavelength, which may then be inserted into equation (vi) per any of the wavelengths, such to calculate D.

* * * * *